United States Patent
Jacq et al.

(10) Patent No.: US 10,527,610 B2
(45) Date of Patent: Jan. 7, 2020

(54) METHODOLOGIES FOR MEASURING ISOPEPTIDASE ACTIVITY IN BIOLOGICAL SAMPLES IN A HIGH THROUGHPUT MANNER

(71) Applicant: Mission Therapeutics Limited, Cambridge (GB)

(72) Inventors: Xavier Jacq, Cambridge (GB); Quentin Gueranger, Cambridge (GB); Jeanine Ann Harrigan, Cambridge (GB)

(73) Assignee: Mission Therapeutics Limited, Cambridge (GB)

( * ) Notice: Subject to any disclaimer, the term of this patent is extended or adjusted under 35 U.S.C. 154(b) by 293 days.

(21) Appl. No.: 15/318,452

(22) PCT Filed: Jun. 15, 2015

(86) PCT No.: PCT/GB2015/051752
§ 371 (c)(1),
(2) Date: Dec. 13, 2016

(87) PCT Pub. No.: WO2015/189646
PCT Pub. Date: Dec. 17, 2015

(65) Prior Publication Data
US 2017/0122935 A1    May 4, 2017

(30) Foreign Application Priority Data
Jun. 14, 2014  (GB) .................... 1410653.8

(51) Int. Cl.
*G01N 33/542*    (2006.01)
*C12Q 1/37*    (2006.01)
*G01N 33/569*    (2006.01)

(52) U.S. Cl.
CPC ............. *G01N 33/542* (2013.01); *C12Q 1/37* (2013.01); *G01N 33/569* (2013.01); *G01N 2333/95* (2013.01); *G01N 2500/02* (2013.01)

(58) Field of Classification Search
None
See application file for complete search history.

(56) References Cited

U.S. PATENT DOCUMENTS 9,382,574 B2 * 7/2016 Chelur ................ C07K 14/00
2007/0166778 A1 7/2007 Jacq et al.
2014/0072992 A1 3/2014 Chelur et al.

FOREIGN PATENT DOCUMENTS

WO    WO 2013/044344 A1    4/2013

OTHER PUBLICATIONS

Horton, R. et al., Anal. Bioch, vol. 360, pp. 138-143 (2007).*
Ekkebus, R. et al., J. Amer. Chem. Soc. vol. 135 pp. 2867-2870 (2013).*
Altun, M. et al., "Activity-Based Chemical Proteomics Accelerates Inhibitor Development for Deubiquitylating Enzymes," *Chemistry & Biology*, vol. 18, pp. 1401-1412 (2011).
Baker, R.T. et al., "Protein Expression Using Cotranslational Fusion and Cleavage of Ubiquitin," *J. Biol. Chem.*, vol. 269, pp. 25381-25386 (1994).
Borodovsky, A. et al., "A Novel Active Site-Directed Probe Specific for Deubiquitylating Enzymes Reveals Proteasome Association of USP14," *The EMBO Journal*, vol. 20, pp. 5187-5196 (2001).
Borodovsky, A. et al., "Chemistry-Based Functional Proteomics Reveals Novel Members of the Deubiquitinating Enzyme Family," *Chemistry & Biology*, vol. 9, pp. 1149-1159 (2002).
Claessen, J.H.L. et al., "Catch-and-Release Proves Applied to Semi-Intact Cells Reveal Ubiquitin-Specific Protease Expression in Chlamydia Trachomatis Infection," *ChemBioChem*, vol. 14, pp. 343-352 (2013).
De Jong, A., et al., "Ubiquitin-Based Probes Prepared by Total Synthesis to Profile the Activity of Deubiquitinating Enzymes," *ChemBioChem*, vol. 13, pp. 2251-2258 (2012).
Falquet, L. et al., "A Human De-Ubiquitinating Enzyme With Both Isopeptidase and Peptidase Activities in Vitro," *FEBS Letters*, vol. 359, pp. 73-77 (1995).
Galardy, P., et al., "Mechanism-Based Proteomics Tools Based on Ubiquitin and Ubiquitin-Like Proteins: Crystallography, Activity Profiling, and Protease Identification," *Methods in Enzymol.*, vol. 399, pp. 120-131 (2005).
Horton, R.A. et al., "A Substrate for Deubiquitinating Enzymes Based on Time-Resolved Fluorescence Resonance Energy Transfer Between Terbium and Yellow Fluorescent Protein," *Analytical Biochemistry*, vol. 360, pp. 138-143 (2007).
Iphöfer, A. et al., "Profiling Ubiquitin Linkage Specificities of Deubiquitinating Enzymes With Branched Ubiquitin Isopeptide Probes", *ChemBioChem*, vol. 13, pp. 1416-1420 (2012).
Larsen, C. et al., "Substrate Specificity of Deubiquitinating Enzymes: Ubiquitin C-Terminal Hydrolases," *Biochemistry*, vol. 37, pp. 3358-3368 (1998).
Layfield, R. et al., "Chemically Synthesized Ubiquitin Extension Proteins Detect Distinct Catalytic Capacities of Deubiquitinating Enzymes", *Analytical Biochemistry*, vol. 274, pp. 40-49 (1999).
Lee, J. I., et al. A Method for Assaying Deubiquitinating Enzymes, *Biological Procedures Online*, vol. 1, pp. 92-99 (1998).
Liu, C. et al., "Purification of a Ubiquitin Protein Peptidase from Yeast With Efficient in Vitro Assays," *J. Biol. Chem.*, vol. 264, pp. 20331-20338 (1989).
Love, K.R. et al., "Ubiquitin C-terminal Electrophiles are Activity-Based Probes for Identification and Mechanistic Study of Ubiquitin Conjugating Machinery," *ASC Chem. Biol.*, vol. 4, pp. 275-287 (2009).

(Continued)

*Primary Examiner* — Heidi Reese

(57) ABSTRACT

The present invention relates to materials and methods for high throughput monitoring of target engagement of isopeptidases, such as deubiquitylating enzymes by, inter alia, small molecule inhibitors. In particular the invention relates to development of high throughput assays to measure isopeptidase activity in biological samples, such as cells, animal tissues, animal tumours, human tissue or patient-derived biopsies.

22 Claims, 13 Drawing Sheets

(56) References Cited

OTHER PUBLICATIONS

McGouran, J.F. et al., "Deubiquitinating Enzyme Specificity for Ubiquitin Chain Topology Profiled by Di-Ubiquitin Activity Probes," *Chemistry & Biology*, vol. 20, pp. 1447-1455 (2013).
Orcutt, S.J. et al., "Bioluminescence Assay Platform for Selective and Sensitive Detection of Ub/Ubl Proteases," *Biochemica et Biophysica Acta*, vol. 1823, pp. 2079-2086 (2012).
Ovaa, H. et al., "Activity Based Ubiquitin-Specific Protease (USP) Profiling of Virus-Infected and Malignant Human Cells," *PNAS USA*, vol. 101, pp. 2253-2258 (2004).
Ovaa, H. et al., "Mechanism-Based Proteomics Tools Based on Ubiquitin and Ubiquitin-Like Proteins: Synthesis of Active Site-Directed Probes", *Methods Enzymol*, vol. 399, pp. 468-478 (2005).
Reverdy, C. et al., "Discovery of Specific Inhibitors of Human USP7/HAUSP Deubiquitinating Enzyme," *Chemistry & Biology*, vol. 19, pp. 467-477 (2012).
Tian, X. et al., "Characterization of Selective Ubiquitin and Ubiquitin-Like Protease Inhibitors Using a Fluorescence-Based Multiplex Assay Format," *Assay and Drug Development Technologies*, vol. 9, pp. 165-173 (2011).
Tirat, A. et al, "Synthesis and Characterization of Fluorescent Ubiquitin Derivatives as Highly Sensitive Substrates for the Deubiquitinating Enzymes UCH-L3 and USP-2," *Anal. Biochem.*, vol. 343, pp. 244-255 (2005).

\* cited by examiner

A. HTRF

B. Western Blot

A. Brain lysates

B. SW48 xenografts

METHODOLOGIES FOR MEASURING ISOPEPTIDASE ACTIVITY IN BIOLOGICAL SAMPLES IN A HIGH THROUGHPUT MANNER

This application is a U.S. national stage filing under 35 U.S.C. § 371 of International Application No. PCT/GB2015/051752, filed on Jun. 15, 2015, incorporated by reference herein in its entirety, which claims the benefit of priority to United Kingdom Patent Application No. 1410653.8, filed on Jun. 14, 2014.

The present invention relates to materials and methods for high throughput monitoring of target engagement of isopeptidases, such as deubiquitylating enzymes by, inter alia, small molecule inhibitors. In particular the invention relates to development of high throughput assays to measure isopeptidase activity in biological samples, such as cells, animal tissues, animal tumours, human tissue or patient-derived biopsies. Furthermore, the high throughput assay can be used to measure isopeptidase in a biological sample which contain microorganisms with or without human or animal cells present. The invention further relates to methods for monitoring pharmaco-dynamic activities of isopeptidase inhibitors in biological samples. Furthermore, the invention relates to methods of demonstrating the activity status of isopeptidases under normal or pathological conditions and, therefore, methods of screening. The invention also provides assays that may be used as a predictive, diagnostic or prognostic tool for pathological conditions which are related to, connected with or due to defective isopeptidase activity. Such an assay may be used to predict pathological outcomes or treatment options. All methods and assays are performed on biological samples.

BACKGROUND TO THE INVENTION

Ubiquitin, a 76 residue polypeptide is used as a posttranslational modification to alter intracellular protein functions in eukaryotic cells. Historically, the ubiquitylation system was identified as an ATP-dependent signal for targeting intracellular proteins for proteasomal degradation (Hershko, A. & Ciechanover, A., 1998, Ann. Rev. Biochem. 67, 425-479; Wilkinson, K. D., 2000, Sem in Cell & Dev. Bio., 11, 141-148 and Varshaysky, A., 2012, Ann. Rev. Biochem, 81, 167-176)).

Ubiquitylation of proteins is a multi-step process requiring the sequential action of three enzymes: ubiquitin-activating enzymes (E1s) activate ubiquitin that is subsequently loaded onto ubiquitin-conjugating enzymes (E2s) and finally, the ubiquitin is covalently linked to a lysine sidechain from the E2s via specific recruitment of the target protein, and facilitation of the transfer by ubiquitin ligases (E3s). Ubiquitin can be linked to target proteins singly, to form monoubiquitin adducts, however, in many cases, the initial ubiquitin is then extended by the covalent attachment (again by E1, E2 and E3 proteins) of additional ubiquitin moieties to form poly-ubiquitin chains. Moreover, as any one of ubiquitin's seven internal lysine residues or its amino terminus can serve as sites for conjugation, the resulting poly-ubiquitin chains can have various, highly distinct topologies with different biochemical and biological functions. While Lys-48 (K48)-linked poly-ubiquitylation of proteins is widely recognised as a critical pathway for protein degradation, many additional roles have been attributed to either poly-ubiquitylation of proteins via non-K48 chains, linear ubiquitin chains as well as mono-ubiquitylation of proteins (Hicke, L., 2001, Nature Reviews Mol Cell Bio, 2, 195-201; Ikeda, F. & Dikic, I., 2008, EMBO Reports, 9, 536-542; Iwai, K., 2012, Trends in Cell Biology, 22, 355-364 and Komander, D. & Rape, M., 2012, Ann. Rev. Biochem, 81, 203-229). In addition to post-translational modification by ubiquitin, a whole family of ubiquitin-like (Ubl) modifications have been described. The degree of conservation between ubiquitin and ubiquitin like factors is somewhat limited at the protein sequence level; however, all members of the family share similar overall three-dimensional structures and highly related mechanisms of conjugation to their respective targets involving E1, E2 and E3 enzymes (Hay, R. T., 2007, Trends in Cell Biology, 17, 370-376; Hochstrasser, M., 2009, Nature 2009 (458) 422-499 and van der Veen, A. G., & Ploegh, H. L., 2012, Ann. Rev. Biochem, 81, 323-357).

Furthermore, since conjugation with ubiquitin or ubiquitin like molecules is a crucial post-translational modification that regulates cellular processes in eukaryotes, it is a system that pathogens encounter when attempting to infect humans and animals. Modification with ubiquitin or Ubl plays a central role in defence systems, for example. Thus, pathogens such as bacteria, viruses, fungi and parasites have evolved to exploit or evade the host systems for their own benefit, in order to maximise their chances of establishing a successful infection (Calistri et al, 2014, Cells, 386-417).

As for other protein post-translational modifications, conjugation of ubiquitin or ubiquitin-like factors to target protein is reversible, this being mediated by isopeptidase enzymes that are often collectively referred to as deubiquitylating enzymes or DUBs. DUBs comprise a large class of intra-cellular peptidases that cleave ubiquitin from polypeptide substrates.

Their substrates can be ubiquitin precursors, ubiquitin adducts, poly-ubiquitin chains, monoubiquitylated proteins or poly-mono-ubiquitylated proteins (Iwai, K., 2012, supra). If ubiquitin-like peptidases are included, over a hundred DUBs are encoded by the human genome. DUBs can be classified into five families: ubiquitin carboxyl-terminal hydrolases (UCH), ubiquitin specific proteases (USPs), ovarian tumour proteases (OTU), MJD (Josephine) and MPN+/JAMM (JAB1/MPN/MOV34 metallo-enzymes). The first four families are cysteine peptidases, while MPN+/JAMMs are metallopeptidases (Reyes-Turcu, F. E., et al, 2009, Ann. Rev. Biochem, 78, 363-397 and Sacco J. J., et al, 2010, IUBMB Life, 62, 140-157). In addition to processing ubiquitin and ubiquitin adducts, some USPs have been shown to selectively process specific ubiquitin-like proteins (for example, USP18 acts on the ubiquitin-like protein ISG15) (Zhang, D. & Zhang, D. E., 2011, J. Interferon and Cytokine Research, 31, 119-130)). In the case of the SUMO family of ubiquitin-like proteins, adducts are reversed by a specialised group of DUBs termed SENPs, all of which are cysteine peptidases, and some of which may also remove NEDD8. (Hay, 2007, supra and Dou, H., et al, 2010, Molecular Cell, 39, 333-345).

Similarly, microorganisms which have the ability to infect eukaryotic organisms (pathogens) have developed enzymes to reverse the conjugation of ubiquitin and Ubl molecules to their target protein, or have evolved strategies to affect the host enzymes. DUBs have been described for microorganisms.

While all DUBs are peptidases, there are considerable differences between their precise mechanisms of action, and there are also major differences in the regulatory mechanisms that modulate DUB selectivity and specificity (Komander, D., et al, 2009, Nature Reviews Mol Cell Bio, 10, 550-563). In this regard, DUBs can be classified into three main categories according to their type of substrate cleavage activity: some generate free ubiquitin from linear substrates, such as poly-ubiquitin chains or ribosomal protein fusions; others liberate ubiquitin from proteins modified post-translationally on lysine residues; while, a third class comprises DUBs that edit poly-ubiquitin chains (Komander et al, 2009). For in depth discussions of DUB mechanism-of-action, we refer the reader to several excellent reviews on this subject (Reyes-Turcu, F. E., et al, 2009, Ann. Rev. Biochem, 78, 363-397; Linder, H. A., 2007, Virology, 362, 245-256; Sun, S. C., 2008, Nature Reviews Immunology, 8(7), 501-511; Hussaun, S. et al, 2009, Cell Cycle, 8, 1688-1697 and Ramakrishna, S. et al, 2011, Cell and Mol Life Sci, 68, 15-26).

Deubiquitylating enzymes may also be called deubiquitinating enzymes, deubiquitinating peptidases, deubiquitinases, ubiquitin isopeptidases, ubiquitin proteases, ubiquitin hydrolases, or DUBs.

The present invention relates to uses, methods and assays involving isopeptidase enzymes. An isopeptidase is an enzyme that catalyses the cleavage of an isopeptide bond, especially that between the terminal diglycine attached to ubiquitin, as well as cleavage of ubiquitin fusion or precursors through peptide bonds. As discussed above, deubiquitylating enzymes are isopeptidases. Other isopeptidases include SUMO (Small Ub modifier) peptidases, ATG8 (Autophagy-related protein 8) peptidase, ISG15 (Interferon-stimulated gene 15) peptidase, NEDD8 (Neural precursor cell, developmentally down regulated 8) peptidase as well as any enzyme-cleaving adducts. Each isopeptidase catalyses the cleavage of an isopeptide bond involving a particular Ubl or Ub, and will be specific for the type of reaction it catalyses.

In order to monitor the activity of isopeptidases, particularly deubiquitylating enzymes, a number of tools and assays have been developed. A number of in vitro assays have been designed to characterise both deubiquitylating enzymes and inhibitors: the list includes many covalent adducts to the carboxy-terminus of ubiquitin (Layfield, R. et al, 1999, Anal Biochem., October 1999, 274(1): 40-49; Lee, J. I., et al, 1998, Biol Proced Online, July 20; 1; 92-99; Liu, C. C. et al, 1989 Dec. 5, J Biol Chem, 264(34): 20331-8; Falquet, L., et al, 1995, FEBS Lett, February 6; 359(1) 73-77; Larsen, C. N. et al, 1998, Biochemistry, March 10; 37(10): 3358-68; Dang L. C., et al, 1998, Feb. 17, Biochemistry, 37(7):1868-79 and Tirat, A., et al, 2005, Anal Biochem, 343(2): 244-55). These assays have led to the biochemical and biophysical characterisation of a large number of DUBs.

A number of ubiquitin-based activity probe assays targeting the catalytic sites of deubiquitylating enzymes in cell extracts have been published in the last decade (Borodovsky, A., et al, 2001, EMBO J., 20(18):5187-96; Borodovsky, A. et al, 2002, Chem Biol, 9(10); 1149-59; Ovaa, H. et al, 2004, PNAS USA, 101(8):2253-8; Hemelarr, J. et al, 2004, J. Proteome Res., 3(2):268-76; Ovaa, H. et al, 2005, Methods Enzymol., 399: 468-78; Galardy, P. et al, 2005, Methods Enzymol., 399:120-31, de Jong, A., et al, 2012, Chembiochem., 13(15):2251-8 and Love K. R., et al, 2009, ACS Chem Biol, 4(4):275-87). Ubiquitin-based activity probe assays have been successfully used to characterise deubiquitylating enzyme inhibitors (Altun, M. et al, 2011, Chem Biol, 18(11):1401-12 and Reverdy, C., et al, 2012, Chem Biol, 19(4): 467-77). Similar activity-based probe assays have also been developed for the characterisation of the activity of ubiquitin-like peptidases as well as non-human ubiquitin-like peptidases (An, H. & Statsyuk, A. V., 2013, J Am Chem Soc, 135(45):16948-62 and Claessen, J. H. et al, 2013, Chembiochem, 14(3):343-52). However, such probe assays are limited since they are low throughput, and as such are time and labour intensive.

Furthermore, a number of high throughput assays have been developed to monitor deubiquitylating enzyme activity in vitro. Many assays currently in use rely on cleavage of linear ubiquitin-fusions, (tetra-Ub, Ub-CEP52, Ub-GSTP1, Ub-DHFR, Ub-PESTc, etc.) that are synthesized recombinantly or chemically (Lee, J I, 1998, Larsen, C. N. 1998 and Baker, R. T et al, 1994, J Biol Chem, 269(41):25381-6). For small scale analysis of deubiquitylating enzyme activity, reaction products are analysed by gel electrophoresis, or are selectively precipitated and analysed by liquid scintillation spectrometry. Gel-based procedures are labour intensive and expensive, and while scintillation counting approaches are quantitative and allow processing of larger numbers of samples compared to gel-based assays, they require centrifugation and recovery of the supernatant. For higher throughput assays, fluorogenic substrates such as Ubiquitin-AMC (Ub-7-amino-4-methylcoumarin) or Ubiquitin-Rhodamine, have been employed, as well as the tetrapeptide z-LRGG-AMC, corresponding to the carboxyl terminus of ubiquitin (Dang, L C, 1998, Supra). Fluorescence Resonance Energy Transfer (FRET) has also been developed for high throughput deubiquitylating enzyme assays (Horton, R. A., et al, 2007, Anal Biochem, 360(1): 138-43). Bioluminescent and fluorescent quenching assays for deubiquitylating enzymes have also been recently developed (Orcutt S. J, et al, 2012, Biochim Biophys Acta., 1823(11): 2079-86 and Tian, X., 2011, 9(2): 165-73). The assays as described use AMC and FRET as detection means, however both assays suffer from the need for specialized custom reagents and equipment, as well as difficulty in adapting to a multi-well plate format from which the endpoints can be read directly. Such assays are used in an in vitro setting, and are biochemical. They do not measure the binding of an activity probe to an enzyme. Whilst these techniques may be suitable for high throughput biochemical assays in the in vitro setting they cannot measure the activity of isopeptidases in biological samples directly. These assays rely on reactions where the enzyme catalyses cleavage of a substrate mimic.

However, high throughput assays enabling the quantification of isopeptidase activity, particularly deubiquitylating enzyme activity in samples of cells or tissues are highly desirable. Such assays are highly advantageous, since they can provide information on the potential inhibition of the enzyme by an inhibitor, can monitor the cellular selectivity of a DUB, can monitor the pharmaco-dynamic activities of one or more enzymes and can be used as a diagnostic and prognostic tool. As such the assays can be used for determining and monitoring the development of one or more enzyme inhibitors, an important step in the drug discovery pathway. None of the currently available methods meets these requirements, and this has hindered or indeed prevented development of drugs which target isopeptidases, particularly deubiquitylating enzymes. The value of using biological samples comprising cellular materials, such as cells, tissues and biopsies is that a more robust picture of how the inhibitor in particular is working in situ and offers a wealth of information when compared to work on isolated enzymes.

The present inventors have recognised this unmet need in relation to the development of drugs that target isopeptidases, particularly deubiquitylating enzymes, and assays that provide diagnostic and prognostic information on isopeptidase activity, particularly deubiquitylating enzyme, activity. They have, therefore, developed a high throughput cell or tissue based assay that allows determination of the activity of isopeptidases. This determination can be performed for normal or pathological cellular material (biological sample). Such an assay has application in determining target engagement by putative inhibitors, monitoring pharmaco-dynamic activities of isopeptidases, and performing diagnostic and prognostic assays on patient-derived biopsies/biological samples.

SUMMARY OF THE INVENTION

In view of the above, it is an object of the present invention to provide a high throughput assay for determining or quantifying the activity of isopeptidases, particularly deubiquitylating enzymes in biological samples such as cells or tissues. The isopeptidase (preferably deubiquitylating enzyme) may be endogenous to the biological sample, or the isopeptidase enzymes may be exogenously supplied, including by the presence of microorganisms in the biological sample.

The present invention relates to the use of an activity probe for the determination of target engagement by isopeptidases in a biological sample in a high throughput format.

The determination of target engagement of an activity probe by an isopeptidase can allow the exploration of various aspects of the isopeptidase in a biological sample. For example, it allows determination of biological activity of that isopeptidase, such that it can be determined if the isopeptidase is within normal parameters or is mutated and/or not functioning properly. These aspects could be used to diagnose or prognose a disease or disorder, including infection. Alternatively, it can be used to determine whether a putative inhibitor is active against an isopeptidase. In relation to an inhibitor, the target engagement can allow determination of potency and pharmacodynamics of an inhibitor of an isopeptidase. The target engagement assay can therefore be put to numerous uses, with some examples listed here.

The present invention furthermore relates to the use of an activity probe for the determination of the effect of a putative inhibitor on an isopeptidase in a biological sample in a high throughput format.

The present invention moreover relates to the use of an activity probe for the diagnosis and/or prognosis of a disease, disorder or condition associated with a defective isopeptidase, in a biological sample in a high throughput manner.

The present invention also relates to the use of an activity probe for the diagnosis and/or prognosis of a disease, disorder or condition associated with the presence of a microorganism.

According to a first aspect of the invention, there is provided a high throughput method for determining the activity of an isopeptidase enzyme in a biological sample, comprising the steps of:
 i) preparing an extract of said sample
 ii) contacting the extract with an activity probe
 iii) including reagents which bind to or interact with the activity probe and/or the enzyme, and generate a detectable signal when the activity probe is bound to the enzyme,
 iv) measuring the detectable signal.

In order to be performed in a high throughput manner or format, it is preferred that the biological sample or the extracts thereof are included on a plate or other suitable array. More preferably, the biological sample or extract thereof are included on a microtitre plate.

The method of this aspect of the invention may determine the activity of one or more isopeptidases present in the biological sample.

It is preferred that the natural substrate for the isopeptidase includes ubiquitin or a ubiquitin-like molecule. It is particularly preferred that the natural substrate for the isopeptidase include ubiquitin. The latter class of isopeptidases are deubiquitylating enzymes.

In one embodiment of any aspect of the invention, one or more isopeptidases are endogenous to the biological sample. Alternatively put, one or more isopeptidases are natural to the human or animal from which the biological sample is taken. In another embodiment, one or more isopeptidases are exogenously expressed in the biological sample. Alternatively put, one or more isopeptidases may be expressed by foreign nucleic acid such as DNA introduced to the biological sample or the animal (resulting in a transgenic non-human animal) from which the biological sample is derived. In yet a further embodiment, the one or more isopeptidases may be natural to a microorganism which is present in the biological sample, but not natural to the human or animal cells which may or may not be present in the biological sample.

According to a second aspect of the invention, the present invention relates to a high throughput diagnostic or prognostic assay to determine the activity of one or more isopeptidase enzymes in a biological sample, comprising the step of:
 i) preparing an extract of said sample
 ii) contacting the extract with an activity probe
 iii) including reagents which bind to or interact with the activity probe and/or the enzyme, and generate a detectable signal when the activity probe is bound to the enzyme,
 iv) measuring the detectable signal.

According to a third aspect of the invention, there is provided a high throughput method for monitoring the target engagement of an isopeptidase enzyme by an inhibitor in a biological sample, said method comprising the steps of:
 i) Treating an animal with said inhibitor and removing said biological sample, or treating said biological sample with said inhibitor
 ii) preparing an extract of said sample
 iii) contacting the extract with an activity probe
 iv) including reagents which bind to or interact with the activity probe and/or the enzyme, and generate a detectable signal when the activity probe is bound to the enzyme,
 v) measuring the detectable signal.

According to a fourth aspect of the invention, there is provided a high throughput method for determining the activity of an isopeptidase in a biological sample in the presence of a putative inhibitor, comprising the steps of:
 i) contacting said biological sample with a putative inhibitor
 ii) preparing an extract of said sample
 iii) contacting the extract with an activity probe
 iv) including reagents which bind to or interact with the activity probe and/or and the isopeptidase, and generate a detectable signal when the activity probe is bound to the enzyme,
 v) measuring the detectable signal.

According to a fifth aspect of the invention, there is provided a high throughput method for determining the pharmaco-dynamics of a putative inhibitor of an isopeptidase, comprising the steps of:
  i) contacting an animal with said putative inhibitor,
  ii) taking said biological sample from said animal,
  iii) preparing an extract of said sample
  iv) contacting the extract with an activity probe,
  v) including reagents which bind to or interact with the activity probe and/or the isopeptidase, and generate a detectable signal when the activity probe is bound to the enzyme
  vi) measuring the detectable signal.

According to a sixth aspect of the invention, there is provided a high throughput method for determining the potency and/or pharmaco-dynamic properties of a putative inhibitor of an isopeptidase, comprising the steps of:
  i) contacting an animal with said putative inhibitor and taking said biological sample from said animal, or contacting said biological sample with a putative inhibitor,
  ii) preparing an extract of said sample,
  iii) contacting the extract with an activity probe,
  iv) including reagents which bind to or interact with the activity probe and/or and the isopeptidase, and generate a detectable signal when the activity probe is bound to the enzyme,
  v) measuring the detectable signal.

According to a seventh aspect of the invention, there is provided a high throughput diagnostic or prognostic assay to determine the activity of one or more deubiquitylating enzymes in a biological sample, comprising the step of:
  i) preparing an extract of said sample
  ii) contacting the extract with an activity probe
  iii) including reagents which bind to or interact with the activity probe and/or the enzyme, and generate a detectable signal,
  iv) measuring the detectable signal.

According to an eighth aspect of the invention, there is provided a high throughput diagnostic or prognostic assay to determine the presence of a microorganism in a biological sample, comprising the step of:
  i) preparing an extract of said sample
  ii) contacting the extract with an activity probe
  iii) including reagents which bind to or interact with the activity probe and/or the enzyme, and generate a detectable signal,
  iv) measuring the detectable signal.

The biological sample may be a cells or tissue sample from a human or animal. The assay may be used to prognose the response to agents, such as anti-microbials, to treat said microorganism. Said microorganism may cause an infection in the human or animal, and be a pathogen.

According to a ninth aspect of the present invention, there is provided a kit for performing the methods of the invention, comprising an activity probe and detection reagents.

BRIEF DESCRIPTION OF THE FIGURES

FIG. 5A depicts Western Blot results of 14 activity probe assays, each monitoring a different isopeptidase as indicated, with and without the probe (+ and −, respectively). FIG. 5B shows two separate Western Blot studies, one each for USP14 and UCHL5.

Various cell types (U2OS, CAL51 and HEK) are tested, without an activity probe, or with the activity probes Ub-VME or Ub-PA. Thus, this shows the optimisation of the activity probe assay using different cell lines or probes.

Figure 6:
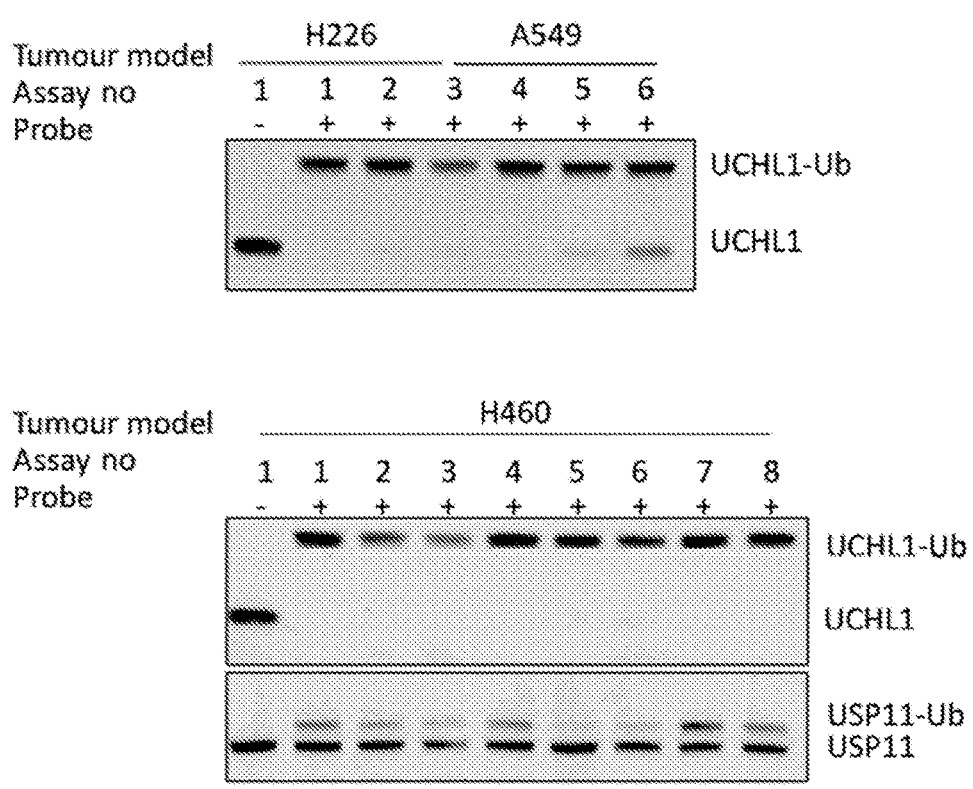
Figure 6:
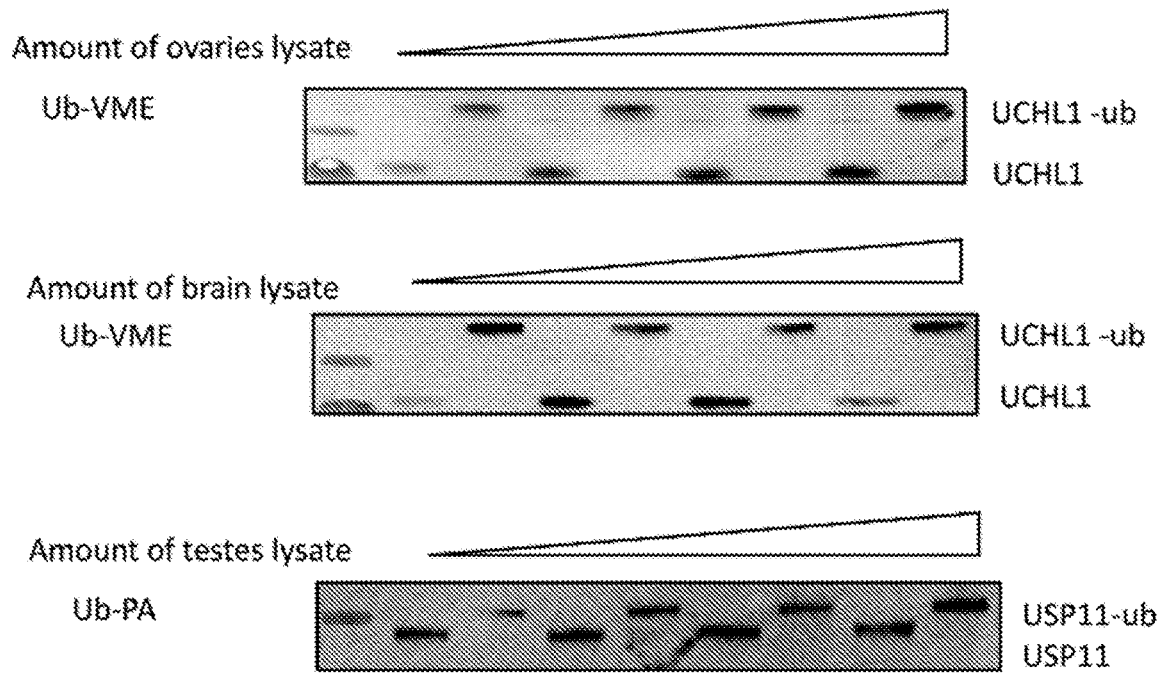

FIG. 6 is an example of Western blot ubiquitin activity probe assays developed in murine tissue models. FIG. 6A depicts two Western blot photographs, the first of which relates to two tumour models H226 and A549. Various tumour samples are tested using the activity probe Ub-VME and its binding to UCHL1 is detected via increase in molecular weight, as shown. In the second western blot photograph, a third tumour model is tested (H460), this time for UCHL1 and USP11 using Ub-VME activity probe. These are xenograft models to monitor USP11 and UCHL1 activity in the tumours. FIG. 6B shows three Western blot photographs, demonstrating the activities of UCHL1 or USP11 in mouse surrogate tissues. The first lane for each is a molecular weight marker. Various tissues are lysed as indicated, and increasing concentrations are used in the studies. Ub-VME is used as the probe for UCHL1 or Ub-PA is used as a probe for USP11 as indicated. Binding of the activity probe is demonstrated by a shift in the molecular weight. These are examples of low-throughput methods. UCHL1 and USP11 are detected using anti-UCHL1 and anti-USP11 antibodies, respectively.

Figure 7:
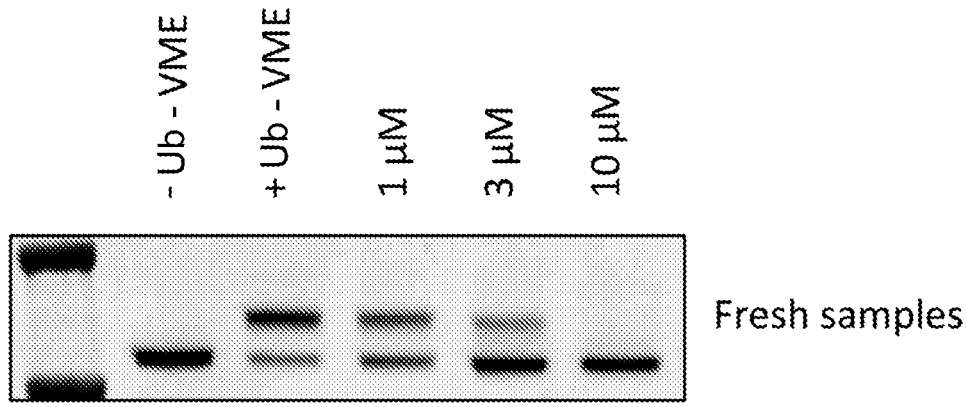
Figure 7:
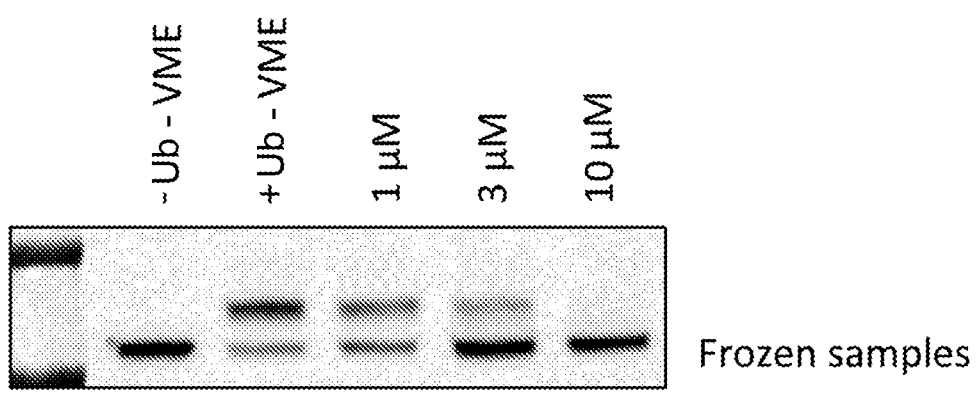
Figure 7:
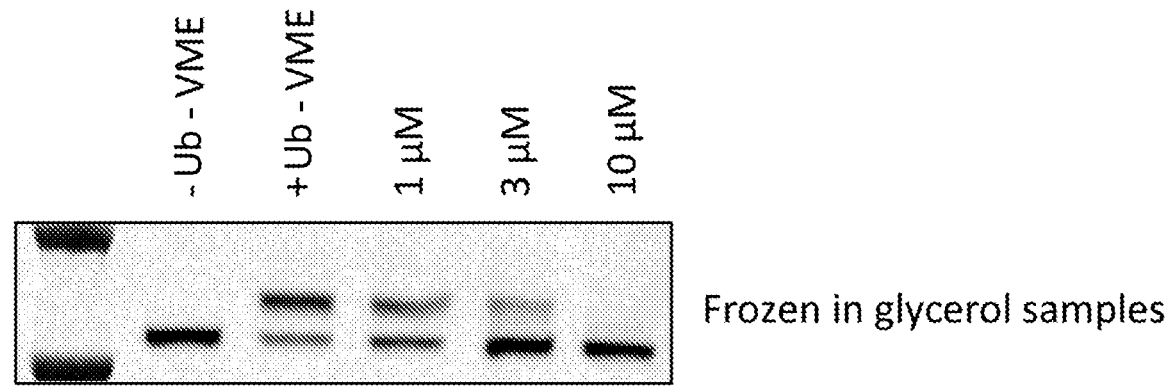

FIG. 7 shows assay optimisations for measuring on-target activity of deubiquitylating inhibitors in cells using activity probes. It also shows stability of lysates and of compound inhibition during freeze/thaw cycles. Photographs of Western blots are provided, and as indicated the cells were fresh, frozen or frozen in glycerol as a cryopreservation agent. U2OS osteosarcoma cells were incubated with DMSO or various concentrations of USP11 inhibitor (depicted MTX) as indicated. Cells were washed and lysed. Lysates were incubated in the absence or presence of an ubiquitin-VME probe. Proteins were separated by SDS-PAGE electrophoresis and transferred to a nitrocellulose membrane. USP11 activity was determined via measurement of a shifted (active, USP11-Ub) relative to non-shifted (inactive, USP11) form of USP11 as indicated by Western blotting with an anti-USP11 antibody. The first lane for each is a molecular weight marker.

Figure 8:
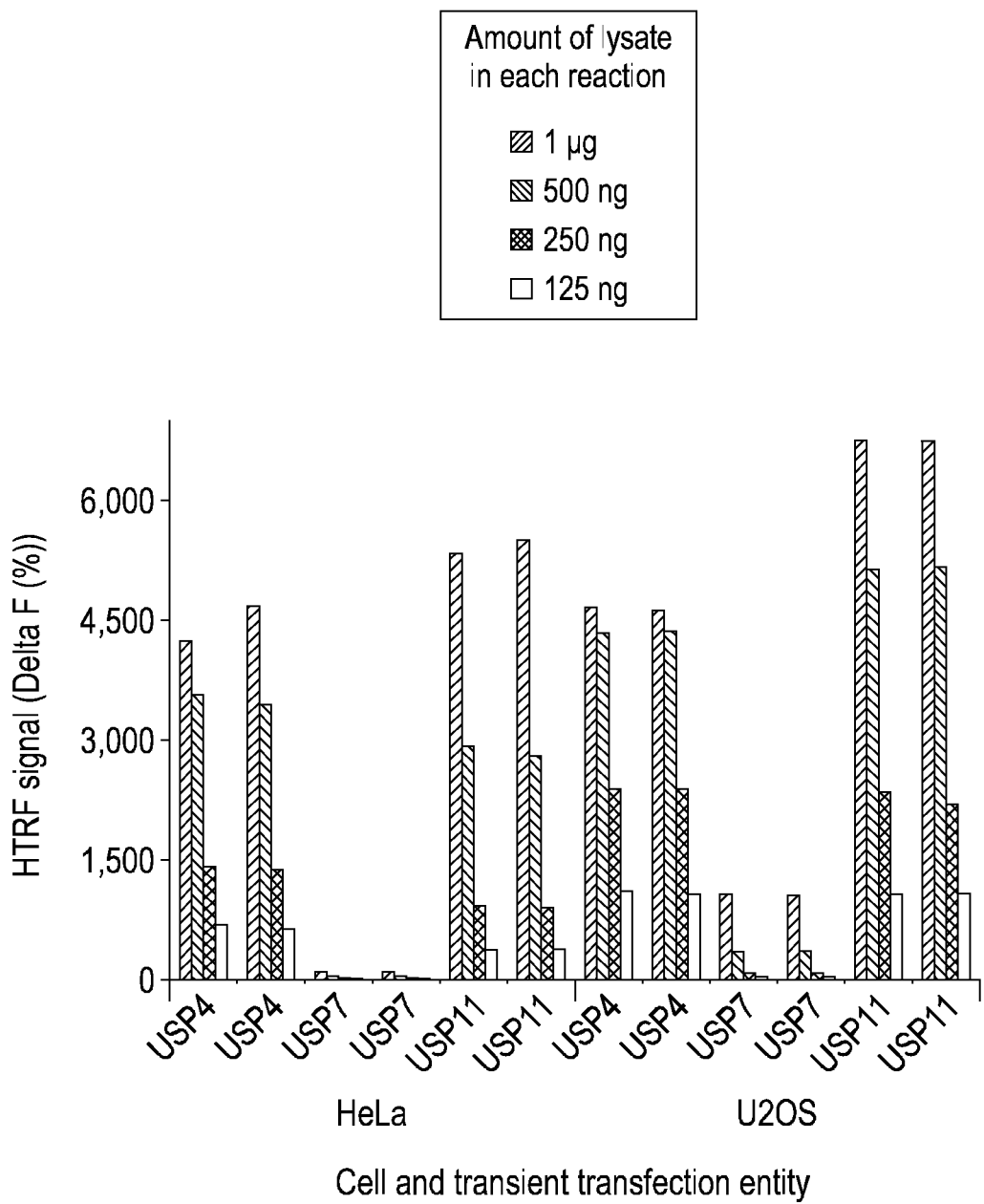

FIG. 8 shows assay optimisation for a high throughput target engagement assay using exogenously expressed deubiquitylating enzymes. A plot of cell type including level of transient transfection of the indicated isopeptidase versus HTRF signal (Delta F %) is presented. Two cell types were used, HeLa and U2OS. The figure illustrates the impact of the lysates dilution on the HTRF signal and its reproducibility. The indicated DUBs were transiently transfected and expressed for 48 h in HeLa or U2OS cells.

Figure 9:
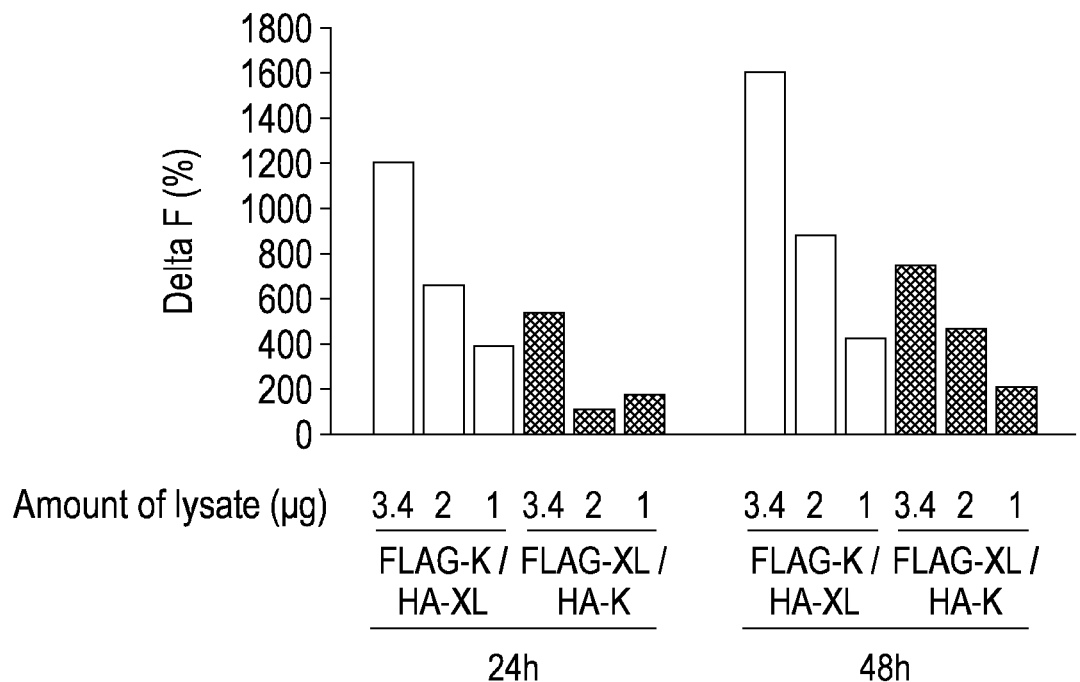
Figure 9:
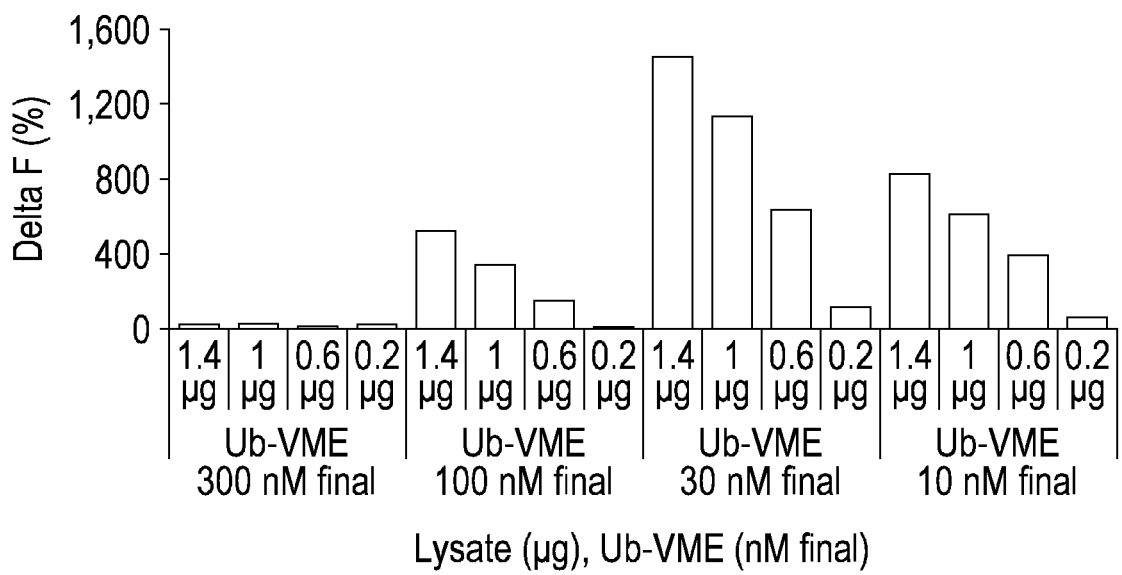

FIG. 9 shows additional assay optimisation for a high throughput target engagement assay using exogenously expressed deubiquitylating enzymes. FIG. 9A depicts the impact of expression duration of USP11 (24 vs 48 h) on the overall HTRF signal as well as the effect of permuting the two detection antibodies. Furthermore, it shows the linearity of the HTRF signal with the amount of lysate used in each sample. FIG. 9B depicts the relationship between the overall amount of lysates from CAL51 cells stably expressing FLAG-UCHL1 and Ub-VME probe used in the assay. These optimisation steps are critical to ensure the best sensitivity and assay window in HTRF assays.

Figure 10:
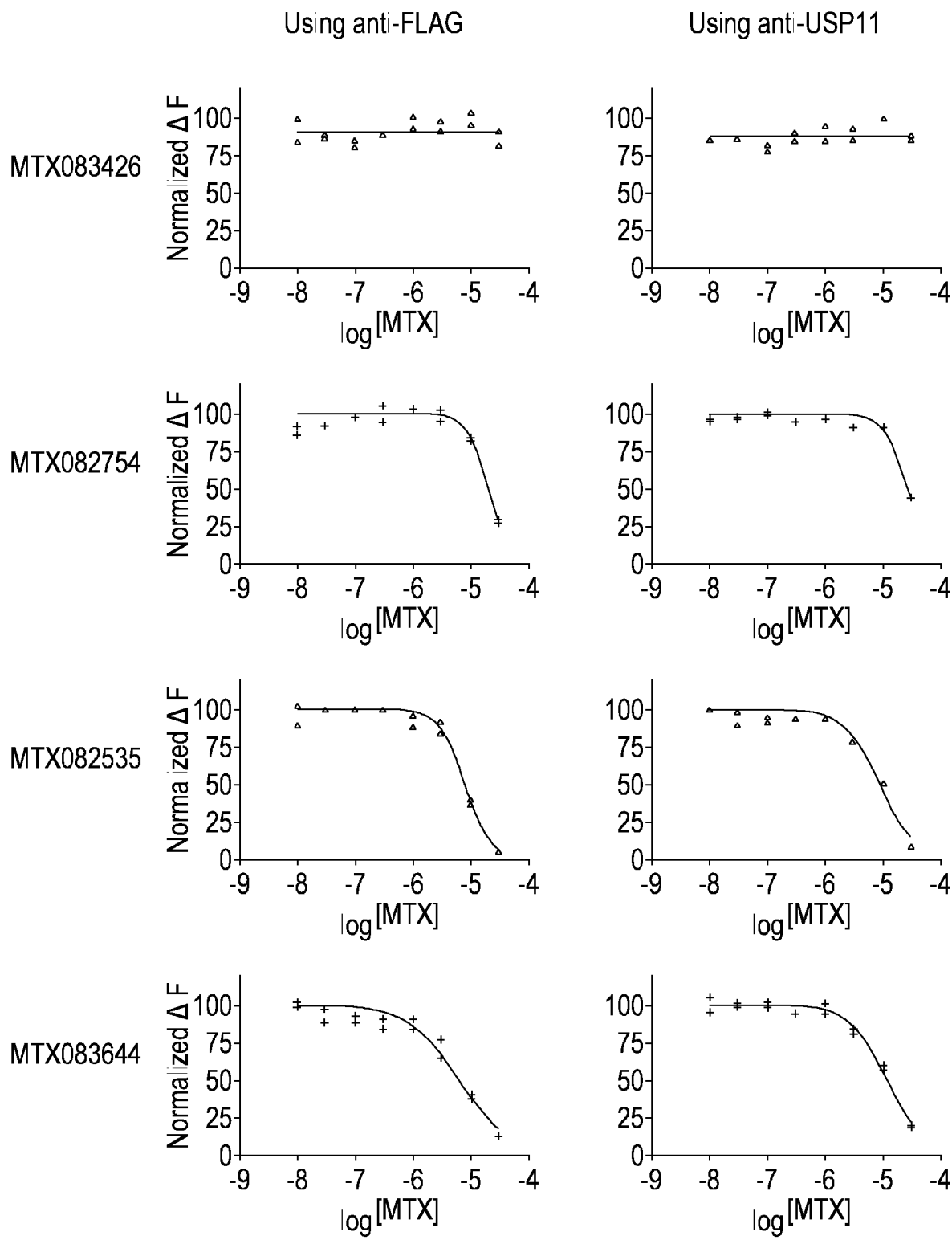

FIG. 10 shows a comparison of high throughput target engagement assay performed in cells expressing exogenously tagged DUBs using antibodies targeting the tag or specific protein, thus the tagged DUB or endogenous, non-tagged and tagged DUB. Putative inhibitors of the isopeptidase are added, these are represented by the MTX number. Typical $IC_{50}$ curves are generated, showing a variety of potencies against USP11. They are obtained by plotting the normalised HTRF signal (Delta F) against the concentration of compound used. The left hand side panel curves were generated using an anti-FLAG antibody, the right hand side panel curves were produced using an anti-USP11 antibody that detects the endogenous USP11 protein as well as the exogenously expressed FLAG-USP11. A comparison of the curves obtained shows that they are remarkably similar.

Figure 11:
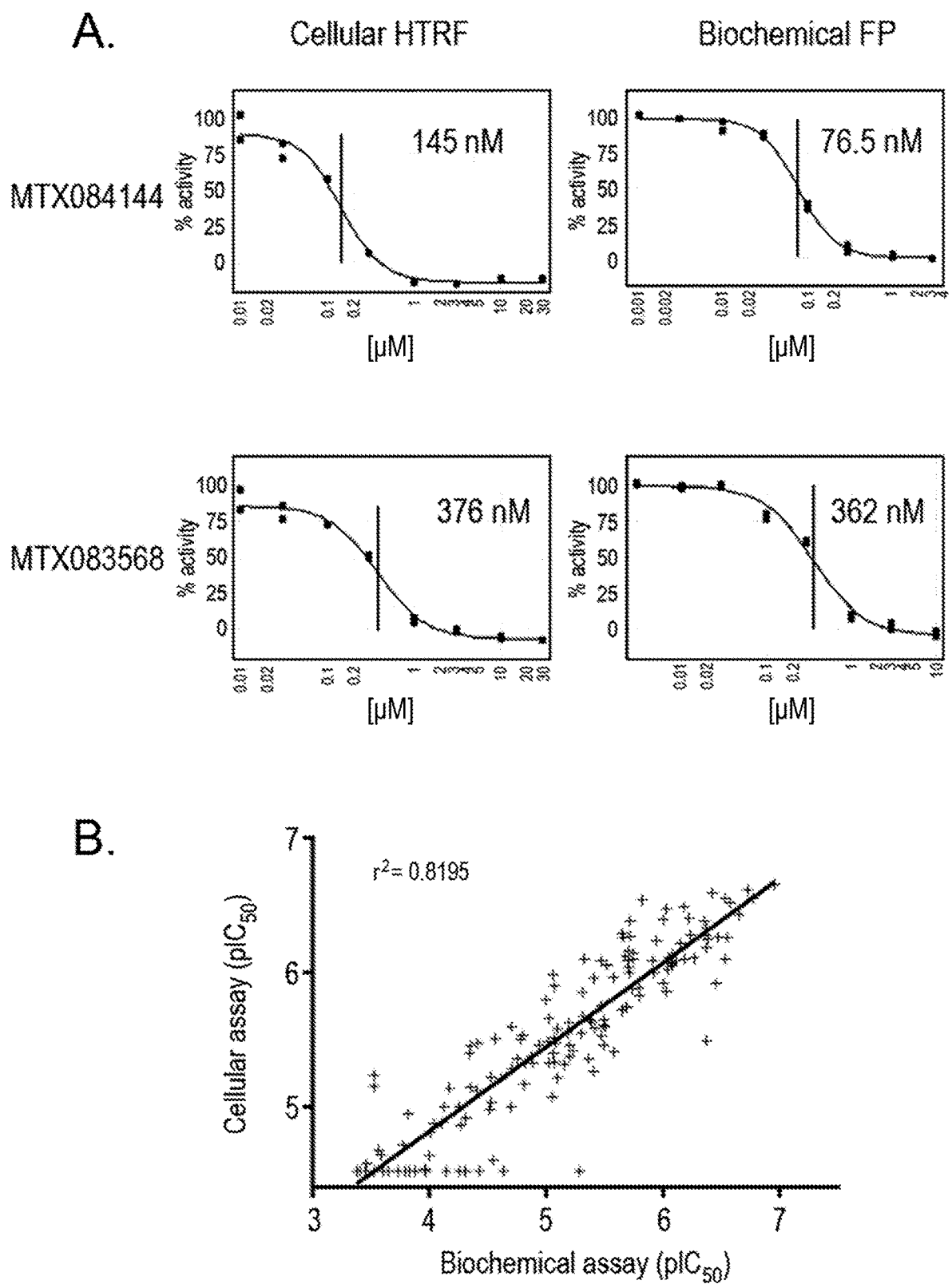

FIG. 11 shows a correlation between a high throughput biochemical assay and high throughput cellular target engagement assay. FIG. 11A represents the study of two small molecule inhibitors, MTX084144 and MTX083568, in two different assays—high throughput cellular target engagement assay (HTRF) and biochemical assay (FP). $IC_{50}$ curves are obtained by plotting the normalised HTRF signal (Delta F) against the concentration of compound used. The $IC_{50}$ value is the concentration at which only 50% of the signal remains. The cellular HTRF activity probe $IC_{50}$ matches the in vitro biochemical fluorescence polarisation (FP) $IC_{50}$: 2 examples indicated. FIG. 11B represents a plot of the biochemical assay $IC_{50}$ versus cellular assay $IC_{50}$. This depicts the correlation between the in vitro biochemical assay $IC_{50}$ and the cellular HTRF—this was obtained for 153 compounds tested for UCHL1 inhibition.

Figure 12:
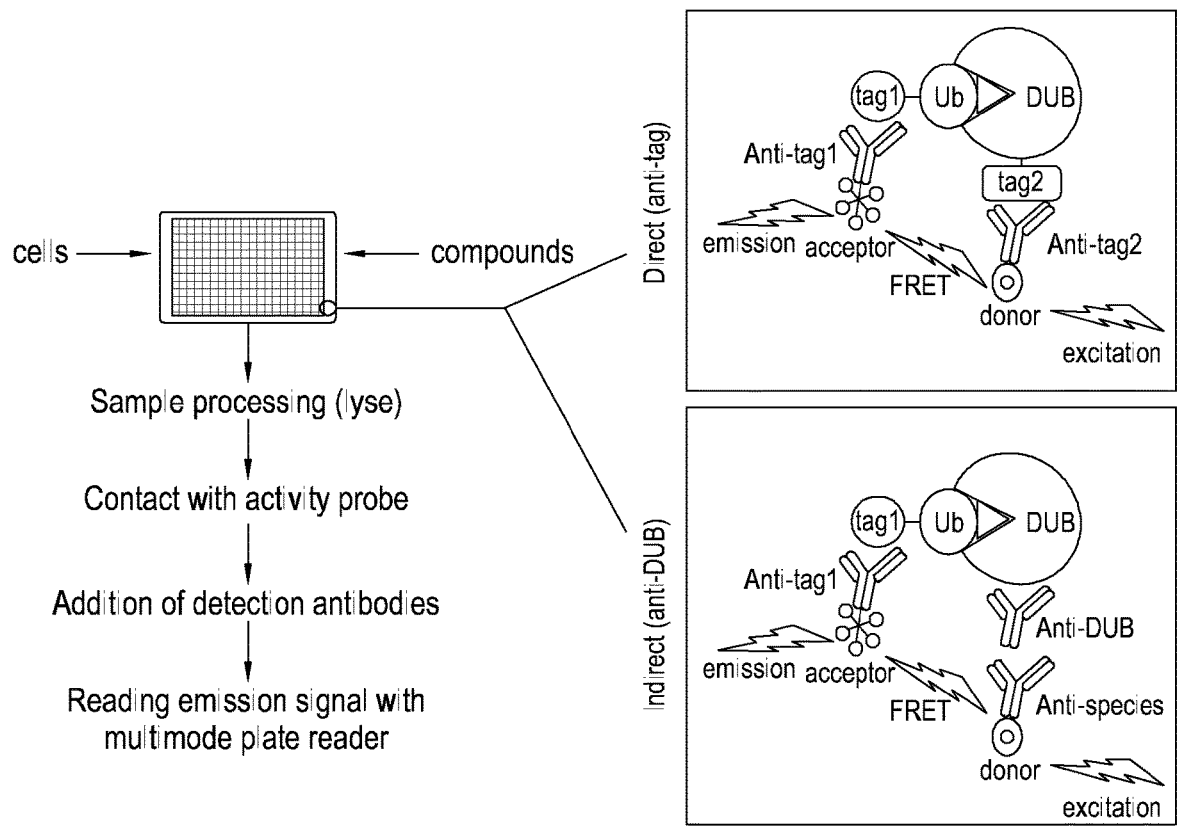
Figure 12:
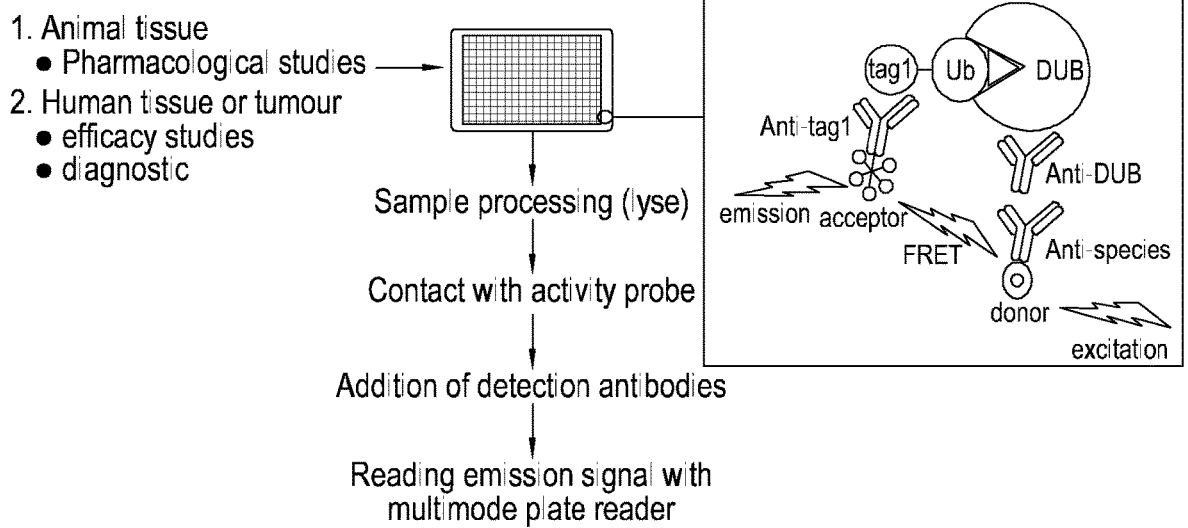

FIG. 12 illustrates the high throughput nature of the assays in various types of biological samples. FIG. 12A depicts target engagement in cell lines, whilst FIG. 12B depicts target engagement in biological samples. As depicted in FIG. 12, the detection of the complex of the activity probe and the isopeptidase can be direct or indirect. This may depend upon whether the isopeptidase is endogenous or exogenous, but can be varied to suit the conditions of the assay.

Figure 13:
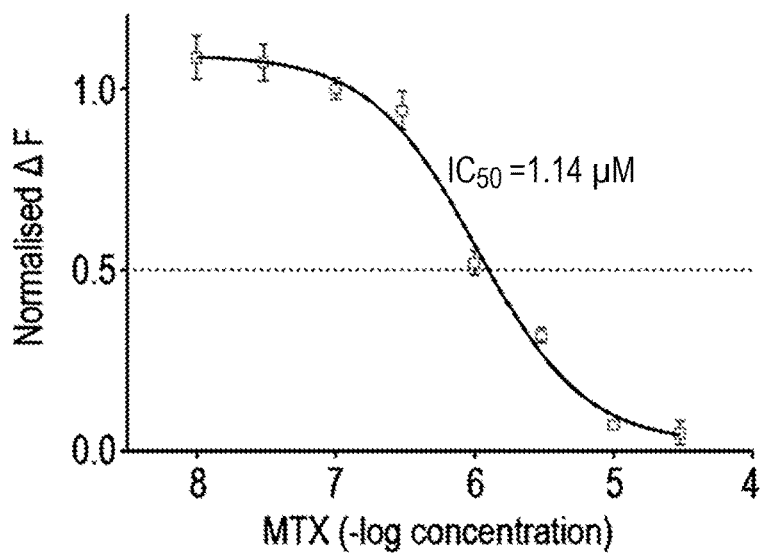
Figure 13:
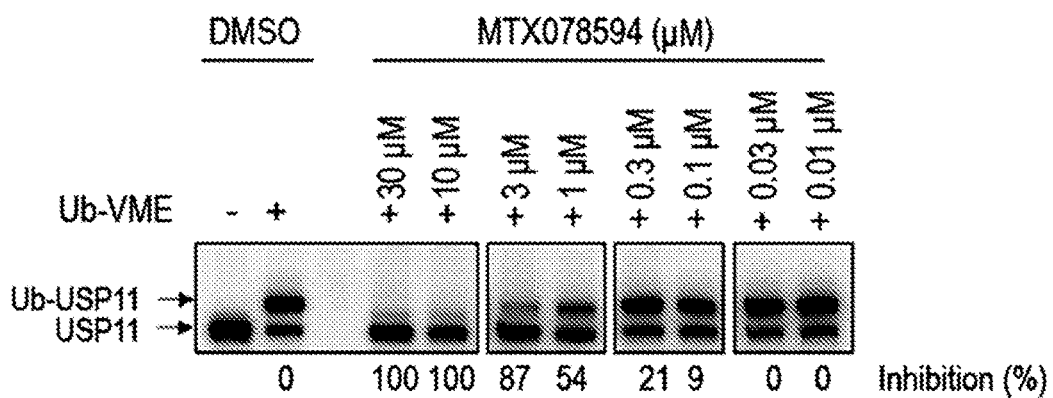
Figure 13:
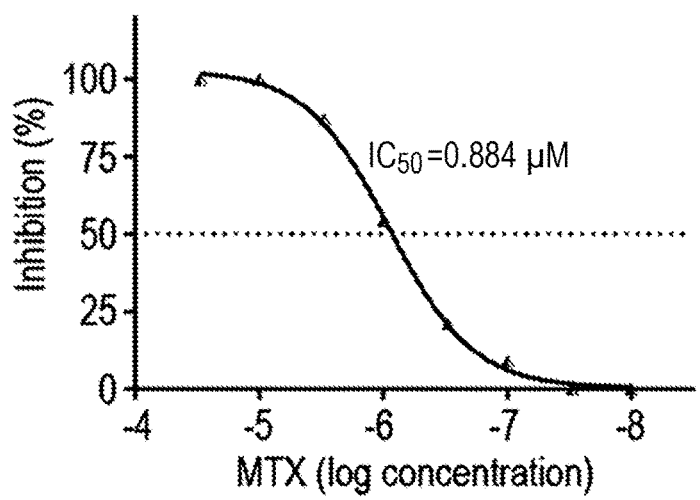

FIG. 13 shows the comparison between HTRF and Western blot activity probe assays for USP11 target engagement by a small molecule inhibitor, MTX078594 in U2OS cells. Endogenous USP11 is tested. FIG. 13A depicts an $IC_{50}$ plot using HTRF and the activity probe Ub-VME. FIG. 13B depicts the Western blot assay, using anti-USP11 antibodies for detection. The probe used was Ub-VME, and this was added to cells to which either DMSO or MTX078594 had been added in the noted concentrations. The shift in the position of USP11 on the gel indicates that the activity probe has bound. These results are also depicted as the plot of MTX concentration versus % inhibition.

Figure 14:
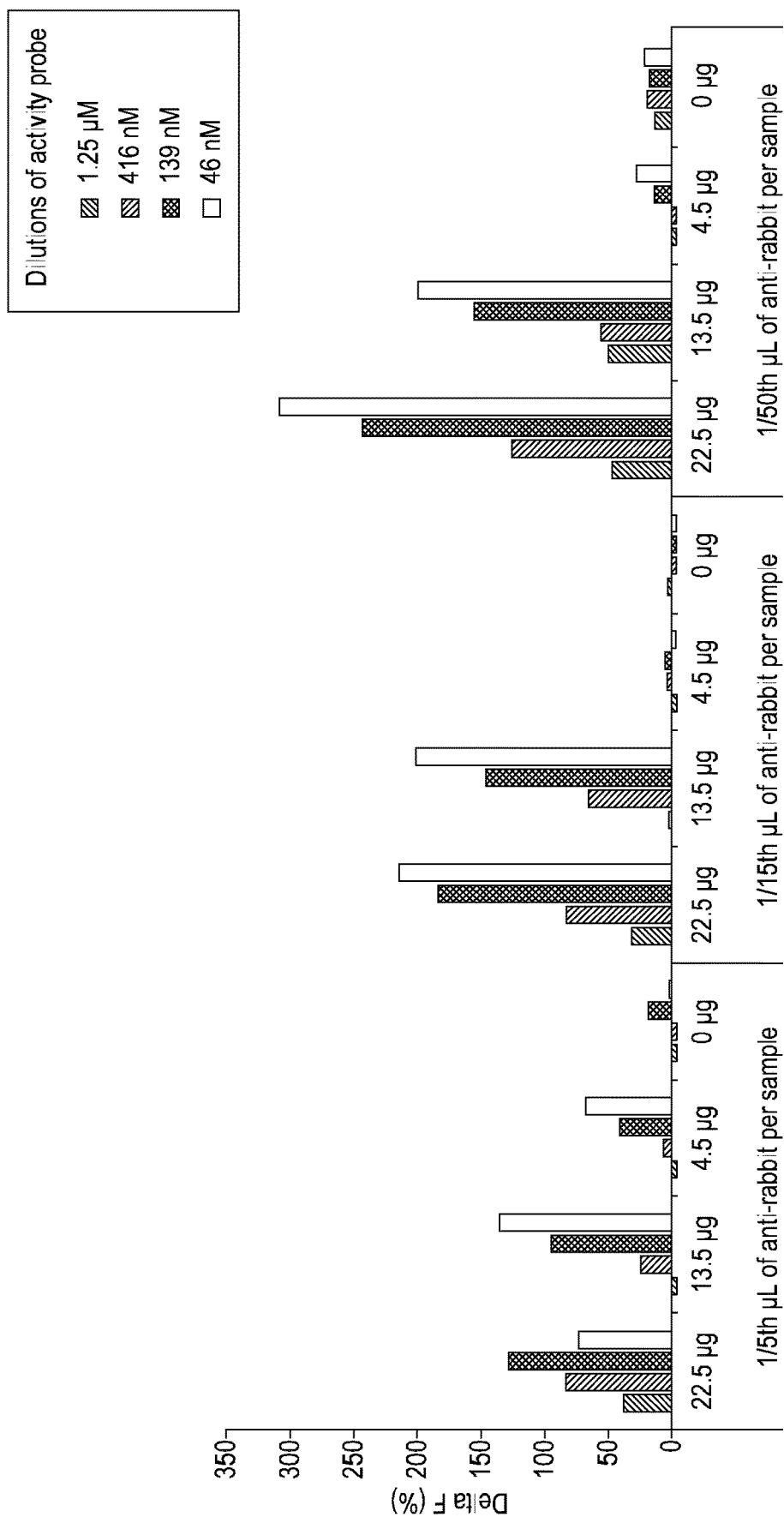

FIG. 14 shows an example of optimisation of the HTRF activity probe assay for endogenous USP5 in HEK 293 cells. In all HTRF assays, it is important to test the stoichiometry of the reagents in order to optimise the assay window and the sensitivity. In this experiment, the parameters tested were the Ub-VME activity probe final concentration (1.25 μM to 46 nM), the amount of lysate (from 22.5 μg to 0 μg) and the concentration of the secondary anti-rabbit antibody ($\frac{1}{5}^{th}$ μL to $\frac{1}{50}^{th}$ μL per sample). This antibody recognises the constant region of the primary antibody against USP5. The values shown are the HTRF signal (% Delta F). This demonstrates the importance of optimising the assay conditions, especially the assay window in this particular instance.

Figure 15:
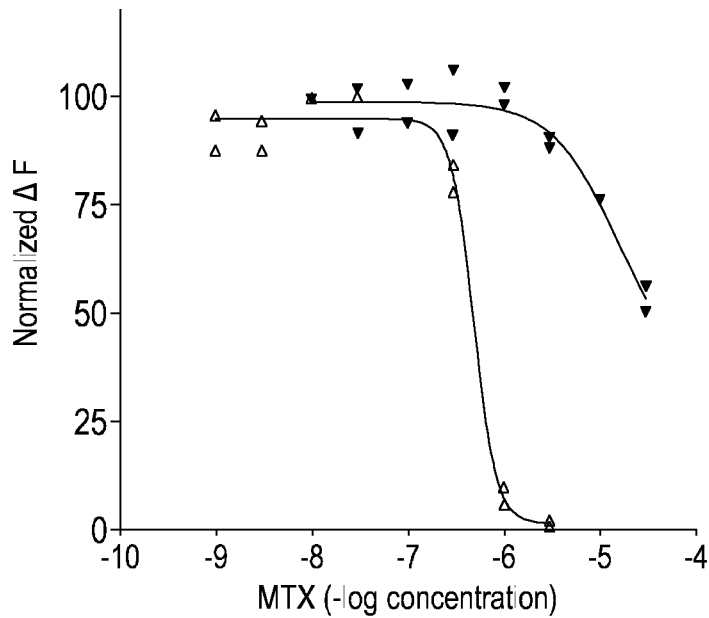
Figure 15:
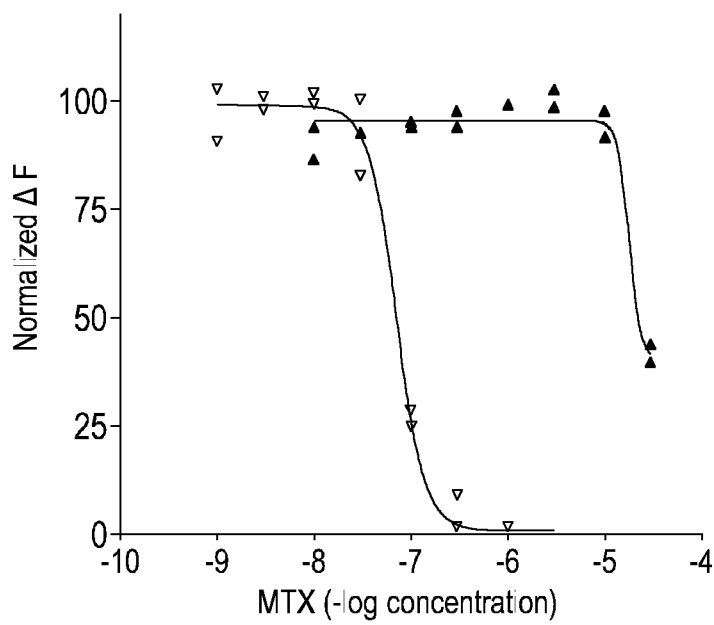

FIG. 15 shows the target (USP5) engagement by two commercially available inhibitors in mouse tissue lysates using HTRF: PR-619 (Sigma Aldrich—SML0430) (closed triangles) and ubiquitin-aldehyde (Boston Biochem U-201) (open triangles). The lysates were freshly generated from the mouse brain (A) or SW48 xenograft (B) tissues and quantified. 10 µg of the lysates were incubated with the known inhibitors for 30 min before adding the activity probe for 60 more minutes after which the primary antibody (anti-USP5), the secondary antibody anti-rabbit-cryptate and the secondary antibody anti-HA-XL665 were added. As expected, ubiquitin-aldehyde is a much more potent inhibitor of USP5 than PR-619.

DETAILED DESCRIPTION OF THE INVENTION

According to a first aspect of the invention, there is provided a high throughput method for determining the activity of an isopeptidase enzyme in a biological sample, comprising the steps of:
  i) preparing an extract of said sample
  ii) contacting the extract with an activity probe
  iii) including reagents which bind to or interact with the activity probe and/or the enzyme, and generate a detectable signal
  iv) measuring the detectable signal It is preferred that a detectable signal is generated when the activity probe is bound to the isopeptidase enzyme. This happens where the reagents that bind to each of the activity probe and enzyme are brought into close proximity, due to the binding of the activity probe.

As used herein, an isopeptidase is an enzyme that catalyses the cleavage of an isopeptide bond, especially that between the terminal diglycine attached to ubiquitin, as well as cleavage of ubiquitin fusion or precursors through peptide bonds. Isopeptidases include SUMO peptidases, ATG8 peptidase, ISG15 peptidase, and NEDD8 peptidase. A particularly preferred class of isopeptidases is deubiquitylating enzymes.

Examples of isopeptidase enzymes include the following:

Human enzymes include, but are not limited to:

The ubiquitin-specific protease (USP/UBP) superfamily; (USP1, USP2, USP3, USP4, USP5, USP6, USP7, USP8, USP9X, USP9Y, USP10, USP11, USP12, USP13, USP14, USP15, USP16, USP17, USP17L2, USP17L3, USP17L4, USP17L5, USP17L7, USP17L8, USP18, USP19, USP20, USP21, USP22, USP24, USP25, USP26, USP27X, USP28, USP29, USP30, USP31, USP32, USP33, USP34, USP35, USP36, USP37, USP38, USP39, USP40, USP41, USP42, USP43, USP44, USP45, USP46 USP47, USP48, USP49, USP50, USP51, USP52, USP53, USP54, USPL1, CYLD);

The ovarian tumour (OTU) superfamily: (Otubain-1 (OTUB1), Otubain-2 (OTUB2), OTUD1, OTUD3, OTUD4, OTUD5, OTUD6A, OTUD6B, OTUD7A, OTUD7B/Cezanne, A20, TRABID, YOD1, VCIP1, HIN1L, FAM10SB/OTULIN);

The Machado-Josephin domain (MJD) superfamily: (ATXN3, ATXN3L, JOSD1, or JOSD2); The ubiquitin C-terminal hydrolase (UCH) superfamily: (BAP1, UCHL1, UCHL3, UCHL5); MPN+/JAMM (JAB1, MPN, MOV34) metallo-enzyme family: (BRCC36, MPND, MYSM1, COPS5, PSMD14, EIF3H, COPS5, EIF3F, PSMD7, AMSH, AMSH-LP, PRPF8);

DeSUMOlyating enzymes (SENPS) family (ULP1, ULP2, SENP1, SENP2, SENP3, SENP5, SENP6, SENP7, DESI1, DESI2, SENP8, USPL1). SENPS are reviewed in Nayak and Müller, 2014, Genome Biology, 15:422.

Homologues of these human enzymes may exist in other organisms.

Fungi are eukaryotic, and therefore posses their own deconjugating enzymes for Ub and Ubl, such as DUBS. Yeast, for example, have numerous DUBs. Fungal DUBs include, but are not limited to:

Ulp1, Ulp2, Ulp3, Ulp4, Ulp5, Ulp6, Ulp7, Ulp8, Ulp9, Ulp10, Ulp11, Ulp12, Ulp13, Ulp14, Ulp15, Ulp16, Atg4, Otu1, Otu2, Yuh1.

Bacterial isopeptidase enzymes include, but are not limited to:

TssM (*Burkholderia pseudomallei*), ChlaDub1, ChlaDUb2 (*Chlamydia trachomatis*), YopP (*Yersina enterocolitica*), YopJ (*Yersina pseudotunerculosis*), SseL (*Salmonella* species), AVrA (*Salmonella enterica*), ELaD (*Escherichia coli*). These are reviewed in Ashida et al, 2014, Nature Reviews Microbiology, Volume 12, 399-413.

Viral isopeptidase enzymes include, but are not limited to:

UL36 (Herpes Simplex Virus type 1 and Marek's Disease virus), UL48 (Human cytomegalovirus), pUL48 (Human cytomegalovirus), pUL36 (PseudoRabies virus), UL36 (PseudoRabies virus), ORF64 (Kaposi-Sarcoma associated herpesvirus—KSHV and Murine gammaherpesvirus 68), RTA (KSHV), BPLF1 (Epstein Barr (EB) Virus), BSLF1 (EB Virus), BXLF1 (EB Virus), vOTU (Crimean-Congo Haemorrhagic fever Virus), PLpro (human coronavirus), PRO (Turnip yellow mosaic (TYM) virus), 98K (TYM virus), PLP2 (Porcine Epidemic Diarrhoea Virus), nsp2 (Porcine Reproductive and Respiratory Syndrome—PRRS Virus), Avp (Adenovirus—ADV), Adenain (ADV), L3 23K proteinase (ADV), SARS-CoV PLpro (Severe Acute Respiratory Syndrome Coronavirus—SARS), MERS-CoV PLpro (Middle East respiratory syndrome coronavirus—MERS), OUT L (variants in Nairobi sheep disease virus, Dugbe virus, PRRS virus, Rice stripe Virus Zhejiang), L(pro) (Foot and Mouth Disease Virus), $MDV^{USP}$ (Marek's Disease Virus), M48 (Murine cytomegalovirus). These are reviewed in Calistri et al, 2014, Cells, 3, 386-417.

Isopeptidases from parasites such as *Schistosoma* and *Plasmodium* are known. Many of these are homologues of human proteins, and include UCHL3 in *Toxoplasma gondii*, *Schistosoma mansoni* and *Plasmodium falciparum*, pfUbp-1, pfUCH54, smUCHL5, smBAP-1, smOTU1, smOTU3, smOTU5a, smOTU6b, smOtubain, smAtaxin-3 and smJosephin.

The isopeptidase of the use, method, assay or kits of the present invention may be selected from any of those enzymes listed above, or any discovered subsequently.

As used herein, the isopeptidase may have ubiquitin or a ubiquitin-like (Ubl) molecule as part of the natural substrate, for example SUMO (small, ubiquitin-like modifiers) It is preferred that the natural substrate for the isopeptidase includes ubiquitin.

As used herein, a high throughput method means that a plurality of tests are conducted in parallel, allowing for rapid determination of results. In general, high throughput methods and/or assays are conducted on plates, which may have wells, such as microtitre plates. The wells of a microtitre plate are usually in multiples of 96, and thus 96 well, 192 well, 288 well 384 well, or even up to 3456 well microtitre plates may be used in any of the methods of the invention. Any suitable number of wells can be used in the high throughput methods or formats, preferably between 96 and 500 wells, more preferably between 96 and 384 wells. It is preferred that the high throughput methods of the present invention are performed on plates, even more preferably plates with 96 or 384 wells. A microtitre plate may also be called a microplate or microwell plate, and is a flat plate with multiple "wells" used as small test tubes. The sample wells are generally arranged in a 2:3 rectangular matrix. The term "plate" also encompasses "array tape", which is a continuous strip of microplates embossed on a flexible plastic tape.

The biological sample can be introduced to the plate at any suitable point in the high throughput method. For example, the biological sample itself can be included on the plate, prior to the preparation of the extract. The cells from the biological sample can be seeded on the plate prior to any processing. Alternatively, the extract can be included on the plate. The latter is particularly preferable if the biological sample is tissue. It is particularly preferred that the extract of the sample is present on a plate by the time the detection step is undertaken, such that the method can be performed in a high throughput manner.

It is preferred that at least one control biological sample/extract is present in the high throughput format or method of the invention. Suitable controls are discussed in relation to each aspect or embodiment of the invention as described herein. For example, a control for a defective or catalytically-inactive isopeptidase may be a wild-type isopeptidase. A suitable control for studies with isopeptidases of unknown activity is a defective or catalytically-inactive isopeptidase. In relation to studies on putative inhibitors, the control may be an isopeptidase resistant/not expected to be inhibited by the putative inhibitor.

In the first aspect of the invention, the activity of an isopeptidase enzyme is determined or measured.

Isopeptidase activity can be defined as follows: In a given biological sample and for a particular isopeptidase, it is the proportion of the isopeptidase population that is capable of binding the activity probe. The inability of binding the activity probe may be the result of, inter alia, pharmacologic inhibition, oxidation, allosteric regulation or genetic mutation that affects the integrity of the active site.

The activity of the isopeptidase is determined via the detected signal generated when the activity probe is bound to the enzyme. It is preferred to measure how much of the complex of activity probe bound to enzyme in a given biological sample compared to a control where no binding is anticipated (for example a catalytically inactive enzyme). It is preferred that the amount of complex formed (amount of activity probe that binds to the enzyme) is compared to a control, for example a catalytically inactive enzyme where no complex will be formed.

Thus, in a preferred embodiment of the invention, the activity probe binds to or interacts with the isopeptidase and forms a complex. The amount of complex in the biological sample is detected and quantified, by methods discussed further below. It is further preferred that the methods of the invention include a control biological sample, and the amount of complex is detected and quantified, in order to provide background or comparative data.

The methods of the invention are conducted on biological samples containing cells, as described below. These cells may be human, animal, or from a microorganism. The biological sample may contain a mixture of human/animal and microorganism cells. A microorganism is an organism that cannot be seen by the human eye, and includes bacteria, fungi such as yeast, viruses and parasites (protozoa). In the methods of the invention, the assay may examine pathogenic microorganisms, i.e. ones that infect humans or animals. Examples of parasitic microorganisms (protozoa) include *Trypanosoma cruzi, Schistosoma mansoni, Toxoplasma gondii, Plasmodium falciparum, P. vivax, P. ovale*, and *P. malariae*.

The methods of the present invention are conducted on biological samples. Such samples are ex vivo biological sample, generally taken from a human or animal body. The biological sample is a sample that contains cells. The sample may comprise cells of the organism sampled, cells of a microorganism which has infected said organism, or a mixture of the two. Suitable biological samples include samples of normal tissues and cells (healthy tissues and cells), samples of tumour cells and tissues, biopsies or aspirates taken from human or animal patients with a suspected defect in isopeptidase/deubiquitylating enzyme activity. Such defect may be suspected in the case of patients with a tumour, cancer including blood-based cancer, congenital disorder, auto-immune disorder, liver dysfunction, infertility, osteopenia, bone marrow defects, growth retardation/development abnormalities, immunodeficiency and/or neurological disease. Alternatively, suitable biological samples includes any biological sample where cells of a microorganism may be present, for example a tissue sample, biopsy, aspirate, or fluid sample, such as blood, lymph, mucus, bronchiolar lavage, sputum, saliva, or urine. Although not part of the present invention, the biological sample may be taken in any suitable manner known to those skilled in the art. Suitable samples for the methods of the invention include samples from any body tissues, including but not limited to tissues and cells from skin, muscle, lung, liver, kidneys, stomach, intestine, ovary, uterus, breast, brain, eye, mucosal membrane, testes, bone or blood. It is preferred that the biological sample contains a sufficient amount of cells, and thus biological samples that do not contain an appreciable number of cells, such a urine, saliva, sweat, tears, mucous, lymph and the like are not generally suitable as biological samples as used herein wherein it is the human or animal isopeptidase under investigation. These biological samples may, however, provide sufficient microorganism cells to perform the assay of the invention. Where the isopeptidase to be assayed is from a microorganism, an additional step of culturing the biological sample under suitable conditions for the microorganism of interest may be undertaken. Such a cultured biological sample may be used in the methods of the invention as a biological sample. Additionally, the human or animal cells from a biological sample may be appropriately cultured prior to use in the assay.

An extract of the biological sample is prepared as part of the methods of the present invention. In order to prepare an extract, lysis of the cells present is preferred. Cell lysis may be achieved by any suitable method known to those in the art. A preferred method of cell lysis is by using a cell-lysis buffer. An example of a cell lysis buffer is a solution comprising a detergent. Detergents have both lysing and solubilising effect, and suitable detergents include, inter alia, CHAPS C3-[(3-cholamidopropyl)dimethylammonio]-1-propanesulfonate) Tergitol® type-NP-40 (nonyl phenoxypolyethoxylethanol), Triton® X-100 (polyethylene glycol p-(1,1,3,3-tetramethylbutyl) phenyl ether), sodium deoxycholate and/or sodium dodecyl sulphate (SDS). It is preferred that the cell-lysis buffer is used such that no denaturation of the cellular proteins is achieved. Those skilled in the art will be familiar with suitable concentrations of detergents to use to avoid denaturation of the cellular proteins. One or more detergents may be used in the cell lysis buffer. Other components of the lysis buffer may include Tris, salts such as sodium chloride and magnesium chloride, glycerol, beta-mercaptoethanol. Other reducing agents such as DTT, DTE and TCEP may be added. It is particularly preferred that protease inhibitor and/or phosphatase inhibitor are added to the lysis buffer.

Should the biological sample be a tissue sample, it is preferred that the tissue sample is treated with a lysis buffer and homogenised in a tissue homogeniser.

Alternatively, the cells may be physically lysed using freeze/thaw techniques, grinding, sonication, homogenisation or mechanical lysis. After lysis or grinding, it is preferred that the sample is centrifuged (or spun) to remove extracellular matrix, cell debris, chromatin and other insoluble material. An alternative method to solubilise chromatin is to digest it enzymatically using Benzonase™, MNase or DNase for example, However, the most preferred method is to use a cell-lysis buffer to prepare the biological sample into an extract.

Once the extract has been prepared, aliquots of the extract may be added to a high throughput plate, such as a microtitre plate, if they are not already included on a plate.

The microtitre plate may comprise one or more extracts, each extract at a different location on the plate. The methods of the invention may thus relate to the testing of one or more biological samples in parallel in a high throughput manner. Thus each of the locations (wells) on the microtitre plate, or alternative high throughput assay format, may contain an extract from a different biological sample. Alternatively, each extract may be present in one or more locations, or one extract may be present at all locations.

Once the sample has been prepared as an extract, and suitably prepared in a high throughput assay format, for example on a plate, an activity probe is added to each extract.

It is preferred that after the extract is contacted with the activity probe, the resultant mixture is incubated. The incubation may be for any suitable length of time. It is particularly preferred that the activity probe and extract are incubated for a period of 5 minutes to 300 minutes, preferably 5 minutes to 240 minutes, more preferably 5 to 180 minutes, even more preferably 5 to 60 minutes, preferably 10 to 40 minutes, most preferably 15 to 35 minutes. It is preferred that the activity probe and extract are incubated for 5, 10, 15, 20, 25, 30 or 35 minutes. Alternatively, the activity probe and the extract are incubated for 30 to 60 minutes, i.e. 30, 35, 40, 45, 50, 55 or 60 minutes.

The activity probe may be any suitable activity probe for an isopeptidase enzyme, and several such entities have been discussed herein, and in the references listed herein. It is preferred that the activity probe comprises a substrate mimic for the isopeptidase enzyme. i.e. the activity probe mimics part or all of the natural substrate for the isopeptidase. It is preferred that the isopeptidase does not catalytically cleave the substrate mimic or activity probe. Thus, the activity probe may be a substrate mimic that is catalytically inactive.

The activity probe may preferably comprise an ubiquitin (Ub) molecule or ubiquitin-like molecule (UBL). Ubiquitin, or "Ub", is a highly conserved 76 amino acid protein expressed in all eukaryotic cells. Preferably, ubiquitin is human ubiquitin. The polypeptide sequence of human ubiquitin is deposited in NCBI database Genpept under accession number P62988.1, with four human genes that encode ubiquitin precursors being deposited as UBB (accession number POCG47), UBC (accession number POCG48), UBA52 (accession number P62987) and RPS27A (accession number P62979). All seven conserved lysines of Ub (K6, 11, 27, 29, 33, 48 and 63) may be used as branching sites for the generation of Ub polymers. Examples of suitable ubiquitin-like proteins include SUMO (Small ubiquitin-like modifier) such as SUMO1, SUMO2 and SUMO3; ISG15 (Interferon-Stimulated Gene-15, also known as UCRP), NEDD8 (Neuronal-precursor-cell-Expressed Developmentally Down-regulated protein-8), FAT10 (human leukocyte antigen F-associated), ATG8 and ATG12 (autophagy 8 and 12), UBL5 (Ubiquitin like protein 5), UFM1 (Ubiquitin fold modifier 1), MUB (membrane anchored Ubiquitin fold) and URM1 (Ubiquitin-related modifier-1). Known or putative Ubls that may be suitable for inclusion in an activity probe are: ISG15, NEDD8 (known deconjugating enzymes are UCHL1, UCHL3, USP21, COP9, and DEN1/NEDP1), FUB1 (MNSF-β or FAU), FAT10, SUMO-1 (deconjugating enzymes include SENP1, SENP2 and SUSP4), SUMO-2 and SUMO-3 (deconjugating enzymes for these include SENP3 and SENP5), Apg 8, Apg 12, Urm 1, UBL5, Ufm1, BUBL1, BUBL2, UBL-1, SF3A120 and Oligoadenylate synthetase. It is preferred that the activity probe may contain any one of the Ubiquitin or Ubiquitin-like molecules selected from the above list. Activity probes containing ubiquitin-like proteins instead of ubiquitin may also be used to evaluate isopeptidases that recognise ubiquitin-like adducts instead of ubiquitin. Activity probes containing ubiquitin may be used to evaluate deubiquitylating enzymes, a particularly preferred option.

The skilled person will be able to select a relevant Ub or Ubl for the activity probe based upon the action of the isopeptidase or deconjugating enzyme of interest.

The ubiquitin or ubiquitin-like protein may be optionally tagged. A tag is a biochemical indicator appended to the ubiquitin, and may be any suitable tag. Thus, the activity probe may comprise a tagged ubiquitin or ubiquitin-like molecule. It is preferred that the tag is selected from the group consisting of:

"Peptide" tags, such as FLAG-tag (DYKDDDDK), HA-tag (YPYDVPDYA), His-tag (HHHHHH), Myc-tag (EQKLISEEDL), Strep-tag (WSHPQFEK), V5 tag (GKPIP-NPLLGLDST), Calmodulin-tag (KRRWKKNFIAVSAAN-RFKKISSSGAL); "protein" tags such as Glutathione-S-transferase-tag, Green fluorescent protein-tag, Maltose binding protein-tag; or "Chemical" tags such as Biotin, DNP (2,4-Dinitrophenol), Chemical coupling reagents (e.g. Cysteines, non-conventional amino acids, etc).

The tag may be bound during detection of the forming of a complex between the activity probe and the isopeptidase enzyme. However, if a tag is not present, then it is possible to directly detect the Ub or Ubl, generally by using an antibody or derivative thereof which is specific for Ub or the Ubl present.

Figure 1:
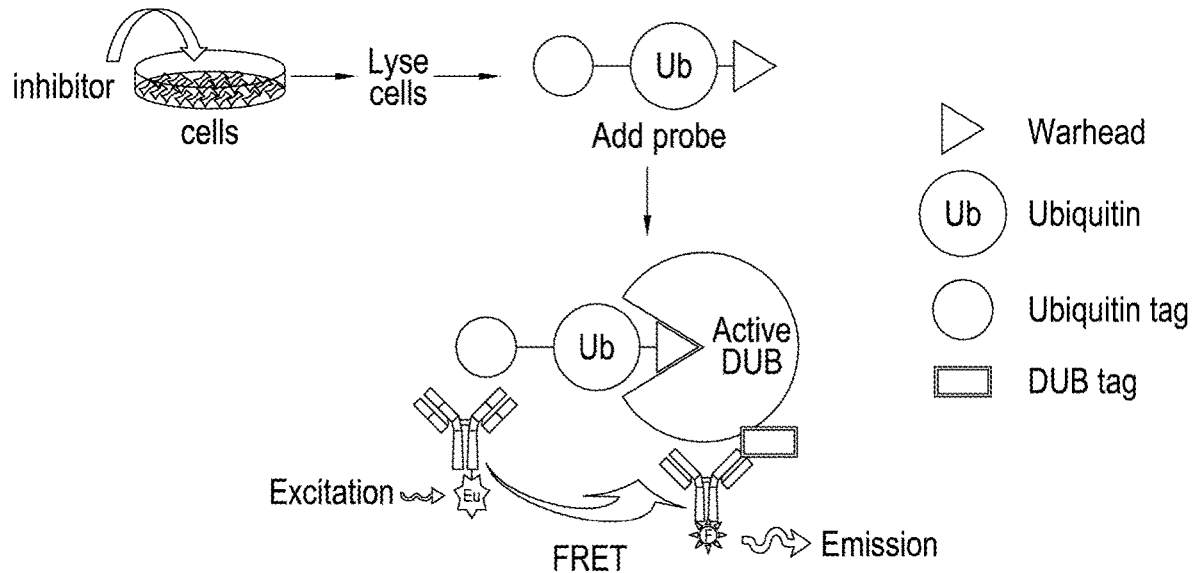
FIG. 1 provides a schematic representation of the assay design for monitoring DUB activity and target engagement in cells expressing exogenously tagged DUBs. One possible method is depicted. A putative or known inhibitor ("inhibitor") is added to dose cells which are, in this depiction, expressing an exogenous tagged-DUB. These cells are subsequently lysed, and an activity probe as shown is added. This probe will bind to DUBs that are catalytically active and available for binding. The binding of the activity probe to the DUB is detected in this depiction by the use of two antigens, one which binds to the ubiquitin tag, and the other that binds to the DUB tag. The first is conjugated to a fluorescence donor such as Europium cryptate (Eu), and the second to a fluorescence acceptor (F), such as XL 665. As shown in the figure, Eu is excited and transfers this to the fluorochrome, F, which emits a signal. This only occurs when the two are in close proximity.
Figure 2:
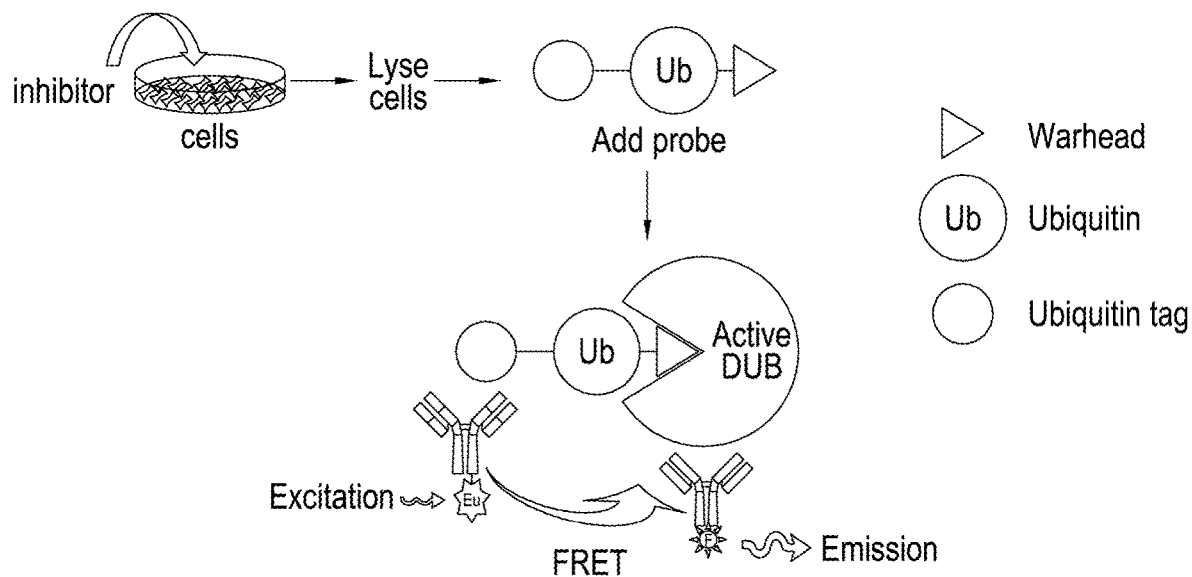
FIG. 2 provides a schematic representation of the assay design for monitoring DUB activity and target engagement in cells expressing endogenous DUBs. One possible method is depicted. A putative or known inhibitor ("inhibitor") is added to dose cells which are, in this depiction, expressing endogenous DUBS. These cells are subsequently lysed, and an activity probe as shown is added. This probe will bind to DUBs that are catalytically active and available for binding. The binding of the activity probe to the DUB is detected in this depiction by the use of two antigens, one which binds to the ubiquitin tag, and the other that binds to the DUB. The first is conjugated to Eu, and the second to F. As shown in the figure, Eu is excited and transfers this to F, which emits a signal. This only occurs when the two are in close proximity.
Figure 3:
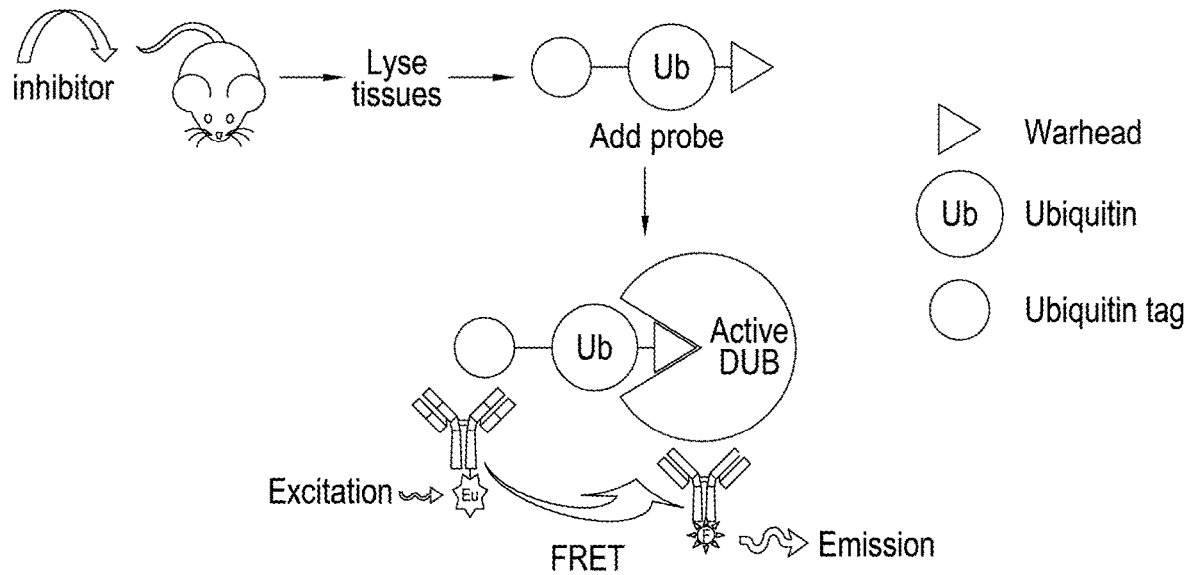
FIG. 3 provides a schematic representation of the assay design for monitoring DUB activity and target engagement in animal tissues or tumours expressing endogenous DUBs. One particular method is depicted. A putative or known inhibitor ("inhibitor") is added to dose an animal, which contains cells which are expressing an endogenous DUB of interest. A sample of cells are taken (not shown) and these cells are subsequently lysed, and an activity probe as shown is added. This probe will bind to DUBs that are catalytically active and available for binding. The binding of the activity probe to the DUB is detected in this depiction by the use of two antigens, one which binds to the ubiquitin tag, and the other that binds to the DUB. The first is conjugated to Eu, and the second to F. As shown in the figure, Eu is excited and transfers this to F, which emits a signal. This only occurs when the two are in close proximity.
Figure 4:
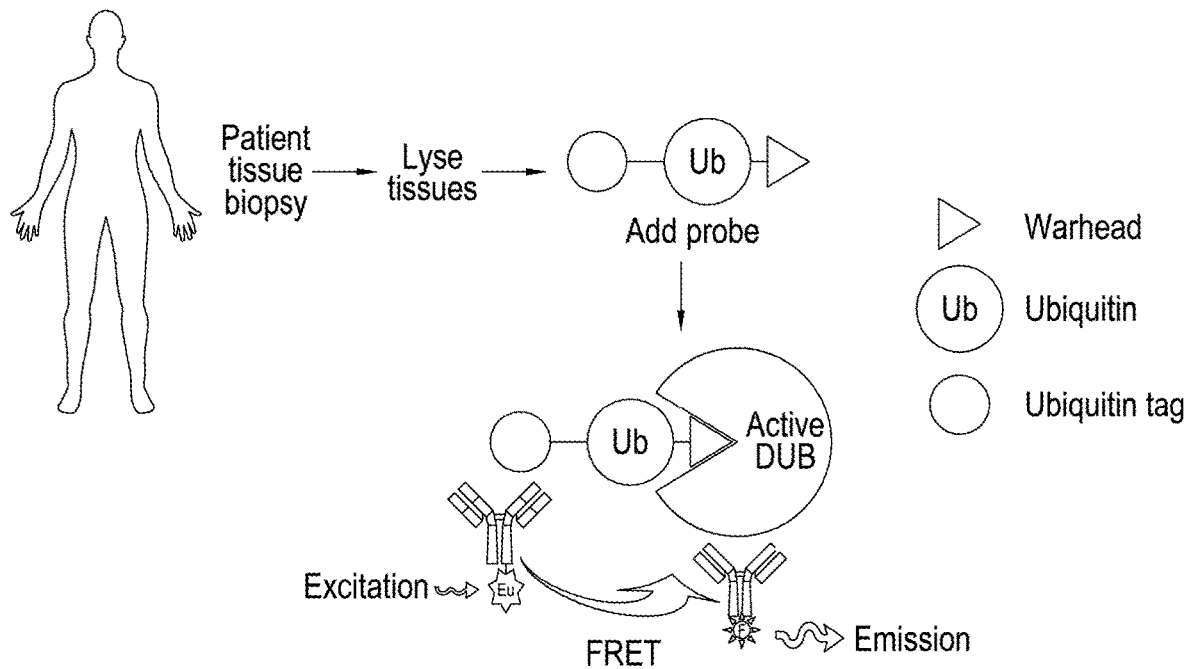
FIG. 4 provides a schematic representation of the assay design for monitoring DUB activity and target engagement in human tissues or tumours expressing endogenous DUBs. One particular method is depicted. A sample or biopsy of cells from a human are taken (not shown) and these cells are subsequently lysed, and an activity probe as shown is added. This probe will bind to DUBs that are catalytically active and available for binding. The binding of the activity probe to the DUB is detected in this depiction by the use of two antigens, one which binds to the ubiquitin tag, and the other that binds to the DUB. The first is conjugated to Eu, and the second to F. As shown in the figure, Eu is excited and transfers this to F, which emits a signal. This only occurs when the two are in close proximity. In this depiction, the quantification of the level of activity probe binding can indicate treatment options for this human patient.

It is preferred that the activity probe comprises a warhead (see FIG. 1). A warhead may consist of a reactive functional group that is able to covalently attach at the active site of the deubiquitylating enzyme or isopeptidase. The warhead is designed to attach at the particular active site of the enzyme of interest. An important parameter in the warhead is the choice of reactive group for covalent labelling of the target isopeptidase enzyme at the enzyme active site. Depending on the mechanism of enzymatic catalysis, different reactive groups can be chosen for covalent capture. The alkylation of nucleophilic residues (Cys, Ser, Thr) present in protease active sites by reactive electrophiles in the warhead can be a useful strategy. Those skilled in the art will be aware of the nature of the active site of the isopeptidase enzyme of interest, and will be able to select a suitable warhead to bind at or close to the active site.

Suitable warheads or reactive groups include alkyl halides (such as chloroethyl, bromoethyl, bromopropyl), Michael acceptors (vinyl methyl ester (VME), vinyl methyl sulfone (VMS), vinyl phenyl sulfone (VSPh), vinyl cyanide (VCN) and propargyl (PA).

The warhead may be present at the C-terminal end of the activity probe, as depicted in FIG. 1. The warhead may be designed to bind to or react with particular residues, notably cysteine residues, in the active site of the isopeptidase.

The warhead may be specific for a single isopeptidase enzyme, or be able to bind or interact with the active site of one or more isopeptidase enzymes, such as VME. Should the warhead be suitable for use in an activity probe for more than one isopeptidase enzyme, it should be noted that complexes with other isopeptidases not of interest will not be detected, since one of the detection reagents is specific for the isopeptidase enzyme itself. Thus, complexes of the activity probe with isopeptidase not of interest will not be detected using this method. Generally, each assay will be looking at the activity of a single isopeptidase in a biological sample, using a specific binding agent for that isopeptidase to ensure only those complexes are detected.

It is it preferred that the activity probe is not subject to catalysis such as cleavage by the enzyme.

In the Examples, several activity probes are utilised, and these are all suitable to use in any of the methods of the invention. These include:

Activity probes suitable for deubiquitylating enzymes include: Tagged-Ub-VME (Ubiquitin-Vinyl Methyl Ester), Tagged-Ub-VMS (Ubiquitin-Vinyl Methyl Sulphone), Tagged-Ub-PA (Ubiquitin-Propargylamide), Tagged-Ub-Cl (Ubiquitin 2-Chloroethyl), Tagged-Ub-Br (Ubiquitin 2-Bromoethyl), Tagged-di-Ubiquitin probes containing various linkages between lysines and glycine isopeptide bonds or branched ubiquitin activity probes as described in (McGouran, J. F., et al, 2013, Chem Biol., 20(12):1447-55 and lphöfer, A., et al, 2012, Chemibiochem, 13(10):1416-20.).

Activity probes suitable for other types of isopeptidase include: HA-SUMO1 VMS (for SUMO peptidases), HA-GABARAP/Apg8p1-VMS (for ATG8 peptidase), HA-ISG15-VME (for ISG15 peptidase), NEDD8-VME (for NEDD8 peptidase), and FAT10-VME.

The isopeptidase enzyme assayed using the methods of the present invention may be endogenous to the biological sample, or may be exogenous. If the biological sample is being tested for endogenous isopeptidase enzymes, no further steps are required in relation to preparing the extract of the biological sample. If, however, the method is looking at an exogenous isopeptidase enzyme, a further step in the method is required prior to preparing an extract of the biological sample, namely introducing the nucleic acid sequence encoding the exogenous isopeptidase enzyme either into the non-human animal prior to removing a sample, or introducing the nucleic acid sequence encoding the exogenous isopeptidase enzyme into the biological sample itself. Those skilled in the art are well versed in suitable techniques to transfect cells or organisms with exogenous nucleic acid. In brief, a plasmid or other suitable vector including the coding sequence for the isopeptidase enzyme and an operably linked promoter can be supplied to the cell. Transfection agents may be required in order to increase the level of transfection, as known to those skilled in the art.

The exogenous isopeptidase enzyme may be any wild-type, non-mutated version of the enzyme, or mutations can be introduced by varying the nucleic acid sequence of the enzyme prior to transfection. Alternatively, the exogenous enzyme can be catalytically inactive, which is particularly useful as a control.

It is preferred that the exogenous isopeptidase is tagged. Suitable tags have been discussed earlier in relation to tagged ubiquitin or ubiquitin-like molecules, and the tagged isopeptidase may include a tag selected from the list given above. Suitable tags thus include FLAG, HA, HIS, Myc, biotin, STREP, TAP, MBP, GST and/or GFP. If both a tagged ubiquitin or ubiquitin-like molecule and a tagged isopeptidase are used in the methods, kits, uses or assays of the invention, it is preferred that the entity used to tag each element (Ub/Ubl or enzyme) is different.

The activity probe is introduced to the extract of the biological sample, and may be incubated as discussed above. If the enzyme is active, the activity probe will bind at the active site. This brings the activity probe and the enzyme in close proximity, and form a complex. It will be understood that the activity probe will only bind to the isopeptidase enzyme if it is available for binding and is catalytically active and functional. Isopeptidase enzymes that are catalytically inactive, damaged, inhibited or mutated at particular key residues, will not be available to bind the activity probe. Thus, use of the activity probe is an elegant way of discovering the activity of a particular isopeptidase enzyme in a particular biological sample. As mentioned previously, the formation of a complex between the activity probe and the enzyme is detected (as discussed below) and compared to the amount of complex formed in a control sample. Said control sample may contain a wild-type (natural, non-mutated) enzyme or a catalytically inactive enzyme.

The binding of the activity probe to the isopeptidase enzyme may be detected by any suitable means, using suitable reagents, preferably detection reagents. The complex formed between the activity probe and the enzyme may be detected. Particularly preferred detection means are the use of two or more reagents; one reagent binds to the activity probe, preferably via the tagged ubiquitin (if present), a further reagent binds to the isopeptidase enzyme. If tagged ubiquitin or Ubl is not present, the reagent may bind directly to the ubiquitin or Ubl. The reagents discussed herein may also be called detection reagents. It is preferred that one of the detection reagents binds to the isopeptidase enzyme, such that the specific complex of isopeptidase and activity probe can be detected. It is preferred, if the isopeptidase enzyme is exogenous, that the detection reagent binds at or close to the tag of the tagged enzyme, if present. Alternatively, the detection reagent will bind to the enzyme itself.

It is preferred that the reagents/detection reagents are binding agents with specific binding affinities for a particular recognition site on their target. Suitable binding agents are well known to those skilled in the art, and include antibodies and derivatives or fragments thereof (Fc, Fab, Fab', ScFv, single domain antibody, $V_H$, or $V_L$ domains) and aptamers.

A first binding agent binds to a recognition site on the activity probe. This recognition site may be the tag or the ubiquitin or Ubl itself. A second binding agent binds to a recognition site on the enzyme. Any suitable recognition site may be used. The first and second binding agents may be the same class of binding agents (i.e., antibodies) or may be different (i.e. one antibody and one aptamer). They both, however, have specific binding affinities for their partners, such that the second binding agent will not bind to a different isopeptidase enzyme, for example.

The binding agents may be labelled in such a way to allow detection of the binding of the probe to the enzyme, via generation of a detectable signal. However, one or more of these binding agents may be unlabelled, in which case, the use of one or more further binding agent(s) which binds to one of the first or second binding agents is also envisioned. These further binding agents may be labelled to permit detection. For example, the second binding agent which is capable of binding to the enzyme could be detected using a further binding agent, which is itself labelled. In one embodiment, as an example, the second binding agent is a mouse monoclonal antibody directed to a particular isopeptidase, and the further binding agent is an anti-mouse antibody. Thus, the binding of the first and/or second binding agent to the complex may be indirectly detected. FIG. 12 depicts examples of each type of binding and detection.

A preferred detection method is the use of Homogenous Time Resolved Fluorescence (HTRF). In this embodiment, one binding agent is labelled with a fluorescence donor, and another binding agent with a fluorescence acceptor. One detects the activity probe and the other detects the isopeptidase (both either directly or indirectly as described above). An example of such a system is shown in FIG. 1. In this case, the donor may be Europium cryptate or Terbium cryptate. The acceptor may be XL 665 acceptor which is a phycobilliprotein (large hetero hexameric edifice of 105 kDa), or d2, which is an organic motif of approximately 1,000 Da.

If HTRF is used to detect the binding of the activity probe to the isopeptidase enzyme, the fluorescence donor is excited using light at a particular wavelength and the fluorescence generated is transferred to the acceptor only if it is in close proximity. Fluorescence from the acceptor can be detected separately to the fluorescence from the donor. Thus, the fluorescence will only transfer from the donor to the acceptor if the activity probe has bound to the isopeptidase enzyme and a complex has been formed, generating a detectable signal.

If Europium cryptate is used, it may be excited by a UV laser light at 317 nm (20 nm bandwidth). The acceptors XL 665 and d2 emit light at 665 nm once the fluorescence from the donor has been transferred.

It is preferred that the detectable signal is generated when a complex forms between the enzyme and the activity probe. This signal may be generated since entities on the detection reagents/binding agents come into close proximity. It will be understood that if no complex if formed, then no detectable signal will be generated and the detection step will detect no signal. Thus, the detection step may detect "no signal" or only detect a signal if present. It is preferred that the measurement of the detectable signal is performed by a plate reader.

The detectable signal can be any suitable signal, such as emission of light (electromagnetic radiation) at a particular wavelength, including fluorescence, and ultraviolet light. The wavelength of the emitted light can be detected by any suitable means, including photosensors and photodetectors. Common detection modes for microplate readers are absorbance (how much light of a particular wavelength is absorbed by the extract), fluorescence intensity, luminescence, time-resolved fluorescence, and fluorescence polarization.

Any suitable detection methodology can be used, for example ELISA (enzyme linked immunosorbent assay), Alpha Lisa, enzyme complementation (e.g. BIFC—Bimolecular fluorescence complementation), alpha-screen, FRET, BRET or label-free affinity technologies. The reagents/binding agents and entities for generating the detectable signal required for these detection means are well known to those skilled in the art—for example ELISA relies on bringing an enzyme and a substrate into close proximity once the activity probe has bound to the isopeptidase. The ELISA enzyme and substrate may be bounds to the binding agents.

The methods of the invention may be used to assay the activity of one or more isopeptidases as described previously. Furthermore, the methods of the invention may be used to determine whether a putative inhibitor has an effect on the activity of the isopeptidase. Thus, according to one aspect of the invention, there is provided a use of an activity probe to determine target engagement in the presence of a putative inhibitor in a high throughput manner in a biological sample.

According to a further aspect of the invention, the method of determining the effect of a putative inhibitor on an isopeptidase may be as described herein in relation to assaying the activity of the isopeptidase, with an additional step of contacting the biological sample with the putative inhibitor prior to preparing the extract. This may be useful when determining the effect of a drug on a disease, disorder or condition, or to determine the effectiveness of a drug on an infection by a microorganism.

Thus, according to a further aspect of the invention, there is provided a high throughput method for determining the activity of an isopeptidase in a biological sample in the presence of a putative inhibitor, comprising the steps of:
  i) contacting said biological sample with a putative inhibitor
  ii) preparing an extract of said sample
  iii) contacting the extract with an activity probe
  iv) including reagents which bind to or interact with the activity probe and/or and the isopeptidase, and generate a detectable signal
  v) measuring the detectable signal.

It is preferred that the detectable signal is generated when the activity probe binds to the isopeptidase and forms a complex.

Such a method may be used to determine the potency of a putative inhibitor. For the purposes of defining this invention, all known inhibitors are also classed as putative inhibitors. Potency is a measure of drug activity expressed in terms of the amount required to produce an effect of given intensity. A highly potent drug evokes a larger response at low concentrations, while a drug of lower potency evokes a small response at low concentrations.

Furthermore, the methods of the invention may be used to determine or measure the pharmaco-dynamics of a putative inhibitor. Thus, according to one aspect of the invention, there is provided a use of an activity probe to determine the pharmaco-dynamic properties of a putative inhibitor in a high throughput manner in a biological sample.

According to one embodiment of the invention, the method of determining the pharmaco-dynamic properties used may be as described herein in relation to assaying the activity of the isopeptidase, with the additional steps of contacting the animal with the putative inhibitor prior to removing a biological sample. In one embodiment, the animal is a non-human animal. In another embodiment, the animal is a human.

Thus, according to a further aspect of the invention, there is provided a high throughput method for determining the pharmaco-dynamics of a putative inhibitor of an isopeptidase, comprising the steps of:
  i) contacting an animal with said putative inhibitor,
  ii) taking said biological sample from said animal,
  iii) preparing an extract of said sample
  iv) contacting the extract with an activity probe,
  v) including reagents which bind to or interact with the activity probe and/or and the isopeptidase, and generate a detectable signal,
  vi) measuring the detectable signal.

It is preferred that the detectable signal is generated when the activity probe binds to the isopeptidase and forms a complex.

In a preferred aspect of the invention, there is provided a high throughput method for determining the potency and/or pharmaco-dynamic properties of a putative inhibitor of an isopeptidase, comprising the steps of:
i) contacting an animal with said putative inhibitor and taking said biological sample from said animal, or contacting said biological sample with a putative inhibitor
ii) preparing an extract of said sample,
iii) contacting the extract with an activity probe,
iv) including reagents which bind to or interact with the activity probe and/or and the isopeptidase, and generate a detectable signal,
v) measuring the detectable signal.

It is preferred that the detectable signal is generated when the activity probe binds to the isopeptidase and forms a complex.

As used herein a "putative inhibitor" is an entity thought to be or known to be an inhibitor of an isopeptidase. The inhibitor can be any suitable entity, including, but not limited to small molecule inhibitors and antibodies or fragments thereof (as defined previously). Putative inhibitors may bind to the active site of the isopeptidase, or bind at a site remote to the active site, but still inactivate the enzyme, for example by causing steric hindrance of substrate binding or cause a conformational change. The methods of the invention can be used to determine if a putative inhibitor is an inhibitor of an isopeptidase. In relation to microorganisms, particularly pathogenic microorganisms, putative inhibitors may be assayed, since this will provide information on whether the drug may be used to treat an infection of the microorganism.

The animal may be any appropriate animal, preferably a mammal such as a rodent (mouse, rat, gerbil, guinea pig, hamster and the like) or other small mammals, such as dogs, primates, cats and the like. It is preferred that the animal is a non-human animal. However, in one aspect the method of the invention may be performed on a human animal in order to study the pharmaco-dynamics of a putative inhibitor in vivo, for example in clinical trials. In one embodiment of the invention, the method may start with the biological sample taken from a human who has previously had administered the putative inhibitor. In an alternative embodiment, the method includes the step of taking a biological sample from a human, as described herein.

Pharmaco-dynamics refers to the relationship between putative inhibitor concentration at the site of action and the resulting effect, including the time course and intensity of therapeutic and adverse effects. Such properties can be determined using the methods of the invention as described herein.

The methods of the invention may additionally or alternatively be used in a method of diagnosis or prognosis. A method of diagnosis or prognosis comprises characterising the endogenous isopeptidase in a biological sample using an activity probe in a high throughput format. Said characterisation can relate to determining the activity of the isopeptidase.

Determining the activity of endogenous isopeptidase is advantageous, since it allows for an indication and/or quantification of a reduction in activity, wherein said reduction in activity may be associated with a disease, disorder or condition. Thus, by determining the activity of the endogenous isopeptidase, it may be possible to diagnose diseases, disorders and conditions. An alternative method of diagnosis is to determine whether there are any active isopeptidases from microorganisms present in a biological sample. Detecting activity from isopeptidases which are solely present in microorganisms can detect the presence of those microorganisms in the biological sample.

Diseases, disorders and conditions relating to mutated, altered, missing or inactive isopeptidases have been discussed previously herein, and include cancers of all body tissues and blood cells. Diseases, disorders and conditions include a tumour, cancer including blood-based cancer, congenital disorder, auto-immune disorder, liver dysfunction, infertility, osteopenia, bone marrow defects, growth retardation/development abnormalities, immunodeficiency and/or neurological disease.

Moreover, having information on the activity of endogenous isopeptidases allows for identification of individuals that will respond in a particular way to a drug or medicament to treat said disease, disorder or condition. Thus, for example, being aware that an individual has a particular defective isopeptidase, results in a prognosis that a particular inhibitor, drug or treatment for the associated disease, disorder or condition should be avoided, since it targets that defective isopeptidase. Conversely, having a deficiency in an isopeptidase can indicate that a particular course of treatment is advisable. For example, it is known that isopeptidases are involved in various DNA damage repair (DDR) pathways, and knowledge that one DDR pathway is defective can allow for targeted treatment against another pathway in order to exploit the principles of synthetic lethality for cancer/tumour cells. Such a diagnostic assay may be called a companion diagnostic assay, since it can determine whether or not a drug will be efficacious for an individual.

The methods of this aspect of the present invention can further relate to the testing of the potency of putative inhibitors against the endogenous isopeptidase, as described previously. Such information on the ability of putative inhibitors to modify the activity of the endogenous isopeptidase allows an informed choice of drugs with which to treat the individual.

Diagnostic and/or prognostic assays may be performed on any suitable biological sample as described herein. It is a requirement that the sample contains cells. Preferably, for the purposes of this aspect of the invention, the biological sample contains cells that are diseased or subject to a condition, i.e. tumour or cancer cells. Such cells may be obtained by any suitable means, including biopsies of solid tumours, cell aspirates from solid tumours and collection of blood-based tumour cells.

In one aspect of the invention, there is provided use of an activity probe in the diagnosis and/or prognosis of a disease, disorder or condition in a high throughput assay in a biological sample.

In a further aspect of the invention, there is provided a high throughput method of diagnosis or prognosis of a disease, disorder or condition associated with a defective isopeptidase enzyme in a biological sample, comprising the steps of:
i) preparing an extract of said sample,
ii) contacting the extract with an activity probe,
iii) including reagents which bind to or interact with the activity probe and/or and the isopeptidase, and generate a detectable signal,
iv) measuring the detectable signal.

It is preferred that the detectable signal is generated when the activity probe binds to the isopeptidase and forms a complex.

In a further aspect, the present invention relates to kits suitable for performing any of the high throughput methods of the invention. Such a kit comprises an activity probe and reagents to detect the activity probe and/or enzyme as hereinbefore described.

All references mentioned herein are incorporated in their entirety for any purpose.

Materials and Methods

1. Standard Ubiquitin-Based Activity Probe Immunoblot Assay

Cells, such as U2OS (ATCC HTB-96), H226 (ATCC CRL-5826), HEK293 (ATCC CRL-1573) or CAL51, were plated in 6-well dishes. The following day, cells were treated with DMSO or the indicated concentrations of inhibitor (depicted as a MTX number) for 1 hour at 37° C. Cells were washed with PBS and lysed in 100 µL of lysis buffer [50 mM Tris, pH 7.5, 150 mM NaCl, 0.1% NP-40, 0.5% CHAPS, 5 mM $MgCl_2$, 5 mM beta-mercaptoethanol (BME), protease inhibitor tablet (Roche—04693159001) and phosphatase inhibitor tablet (Roche—04906837001). Cells were scraped in lysis buffer and incubated for 30 min on ice. Lysates were centrifuged at 8,000 rpm for 5 min at 4° C. and the supernatant transferred to a new tube. Protein concentration was determined by using Coomassie Plus Protein Assay Reagent (Life technologies—23238) with BSA as a standard according to the manufacturer's recommendation. Lysates (20 µg) were diluted in lysis buffer and incubated in the absence or presence of 500 ng HA-Ahx-Ahx-Ub-VME activity probe (UbiQ—035) or Ubiquitin-Propargylamide (UbiQ—057) in a final assay volume of 20 µL. Reactions were incubated for 60 min at room temperature and terminated by the addition of SDS-loading buffer and boiled for 5 min. Proteins were separated by SDS-PAGE (Life technologies—NP0355BOX) and transferred onto nitrocellulose. Immunoblotting antibodies used are listed in table 1. Anti-mouse HRP and anti-rabbit HRP secondary antibodies are from Fisher Scientific—31430 and—31460 respectively. The chemiluminescent substrate is from GE Healthcare—RPN2109. The GE LAS4010 imaging system was used to acquire the luminescent signal that was quantified using the Image Quant TL software (GE Healthcare Life Sciences).

2. Expression and Purification of UCHL1

The UCHL1 construct was PCR amplified and cloned into a pFLAG-CMV-6a vector (Sigma-Aldrich) with an N-terminal FLAG tag. HEK293T cells were transfected with FLAG-UCHL1 using TransIT-LT1 transfection reagent (Mirus-2306) according to the manufacturer's instructions. Cells were harvested 40 hours after transfection. Cells were washed once with PBS and scraped in lysis buffer (50 mM Tris, pH 7.5, 150 mM NaCl, 3 mM EDTA, 0.5% NP40, 10% glycerol, 5 mM BME, protease inhibitors (complete mini, Roche) and phosphatase inhibitors (PhosSTOP mini, Roche). Lysates were incubated for 30 min on ice and centrifuged at 1200 rpm for 10 min at 4° C. Soluble supernatant was added to FLAG affinity resin (EZview Rad ANTI-FLAG M2 affinity gel, Sigma-Aldrich) equilibrated in low salt buffer (20 mM Tris, pH 7.5, 150 mM NaCl, 0.5 mM EDTA, 5 mM BME) and incubated at 4° C. for 3 hours rotating. The resin was spun at 2000 rpm for 2 min and the supernatant was removed. The resin was washed two times with low salt buffer and one time with high salt buffer (20 mM Tris, pH 7.5, 500 mM NaCl, 0.5 mM EDTA, 5 mM BME, protease inhibitors (complete mini, Roche) and phosphatase inhibitors (PhosSTOP mini, Roche). To elute the bound UCHL1, elution buffer (10 mM Tris pH 7.5, 150 mM NaCl, 0.5 mM EDTA, 10% glycerol, 0.5% NP40, 5 mM BME, 0.15 mg/ml 3×FLAG peptide (Sigma-Aldrich)) was added to the resin and incubated at 4° C. for 2.5 hours rotating. The resin was centrifuged at 4000 rpm for 30 seconds, and the supernatant containing purified FLAG-UCHL1 was removed and stored at −80° C.

3. FLAG-UCHL1 Biochemical Assay

Reactions were performed in duplicate in black 384 well plates (small volume, Greiner 784076) in a final reaction volume of 21 µL. UCHL1 was diluted in reaction buffer (20 mM Tris, pH 7.5, 100 mM NaCl, 0.05% Tween 20, 0.5 mg/ml BSA, 5 mM BME) to the equivalent of 0.05 µL/well. Buffer was optimised for optimal temperature, pH, reducing agent, salts, time of incubation, and detergent. The enzyme was incubated with 1 µL of the compound diluted in 50% DMSO for 30 minutes at RT prior to the reaction initiation. Reactions were initiated by the addition of 50 nM of TAMRA labelled peptide linked to ubiquitin via an isopeptide bond as fluorescence polarisation (FP) substrate (UbiQ-012). Reactions were incubated at room temperature and read every 2 min for 120 min. Readings were performed on a Pherastar Plus (BMG Labtech). A Excitation 540 nm; A Emission 590 nm. The determination of the $IC_{50}$ is done by plotting the FP signal (signal at 120 min—signal at 0 min) for each compound dilution against the compound concentration.

4. Preparation of Tissue Lysates.

Samples were removed from the −80° C. freezer and thawed on ice. Using clean forceps and scalpel, tissues were carefully sliced from the main sample where appropriate. Between samples, forceps were cleaned with 70% ethanol and a new scalpel was used for each tissue. Eppendorf tubes were weighed prior to and following addition of the tissue and tissue weight calculated. Three volumes (w/w) of lysis buffer were added to the tissue (50 mM Tris pH 7.5, 150 mM NaCl, 0.1% NP-40, 0.5% CHAPS, 5 mM $MgCl_2$, 10% Glycerol, 5 mM BME. For 10 mL of buffer, 1 tablet of protease inhibitor (Roche #04693159001) and phosphatase inhibitor was added (Roche #04906837001). Tissues were homogenised for 45 sec. in a tissue homogeniser (Retsch MM 400) using 3 small discs on frequency 25. Supernatants were transferred to a new Eppendorf being careful to avoid any solid material or beads. Lysates were centrifuged at 13,000 rpm in microfuge for 15 min at 4° C. Supernatants were removed and transferred to new tube. Lysates were diluted 2-fold with lysis buffer and quantitated using a Bradford assay (Life technologies—23238).

5. Standard HTRF Ubiquitin-Based Activity Probe Assay

U2OS or HEK 293 cells grown in DMEM+10% FCS+ antibiotics were seeded in a 96-well plate at 10,000 cells per well and reverse transfected with 40 ng of, for instance, FLAG-USP11 or FLAG-USP4 or FLAG-USP7 (pFLAG-CMV-6a backbone) using Trans IT (MIRUS—2306) transfection reagent according to the manufacturer recommendations. The catalytically inactive FLAG-USP11 was transfected in 4 wells as a negative control. After 48 h, the compounds were diluted in medium and added to the cells for 1 h at 37° C. Cells were washed twice with PBS, lysed in 20 µL of cold lysis buffer ((50 mM Tris, pH 7.5, 150 mM NaCl, 0.1% NP-40, 0.5% CHAPS, 5 mM MgCl2, 5 mM BME, protease inhibitor tablet (Roche) and phosphatase inhibitor tablet (Roche)) and left on ice for 30 min. The lysates were quantified using a Bradford assay to monitor potential toxicity of small molecules. In a white small volume 384 well plate (Greiner #784075), 5 µL of lysate was dispensed (in duplicate) and combined with 5 µL of the Ub-VME probe (UbiQ-35) diluted to 100 nM in the HTRF buffer (20 mM Tris pH 7.5, 100 mM NaCl, 0.05% Tween 20, 0.5 mg/ml BSA, 5 mM BME) and incubated for 30 min at RT. Detection antibodies (10 µL) were diluted in detection buffer (400 mM KF, 50 mM HEPES pH 7.5): 0.033 µL of the anti-FLAG cryptate antibody (Cisbio #61FG2KLA) and 0.1 µL anti HA-XL antibody (Cisbio #610HAXLB). The plates were sealed and incubated O/N at 4° C. The next morning, plates were read immediately using the PHERAstar (BMG), and the Delta F calculated:

$$\text{Delta } F = 100 \times (\text{ratio}^{sample} - \text{ratio}^{negative\ control}) / \text{ratio}^{negative\ control}$$

$$\text{Ratio} = 10{,}000 \times (\text{fluorescence emission at 665 nm/fluorescence emission at 620 nm})$$

The determination of the $IC_{50}$ is done by plotting the HTRF signal (% Delta F normalised against the vehicle treated sample) for each compound dilution against the compound concentration.

Alternative 1: for the USP11 assay, the anti-USP11 antibody (Bethyl # A301-613A) together with an anti-rabbit-cryptate (Cisbio #61PARKLA)—1.3 ng per well for both—is used in replacement of the anti-FLAG-cryptate.

Alternative 2: for the UCHL1 assay, CAL51 cells stably expressing FLAG-UCHL1 are used (see below). The cells were seeded at 45,000 cells per well on the day preceding the assay.

Alternative 3: for the USP5 assays, 0.05 µL of the anti-USP5 antibody (Bethyl # A301-542A) together with 0.024 of the anti-rabbit-cryptate (Cisbio #61PARKLA) is used in replacement of the anti-FLAG-cryptate 6. CAL51 Cell Lines Cal-51 cells stably expressing a tet inducible FLAG-UCHL1 (wild-type or catalytically inactive version) fusion protein was created using a lentiviral vector (pLENTI-TetCMV-RsV puro). The transformed cells were selected using blasticidin (5 µg/mL) and puromycin (0.625 µg/mL).

Figure 5:
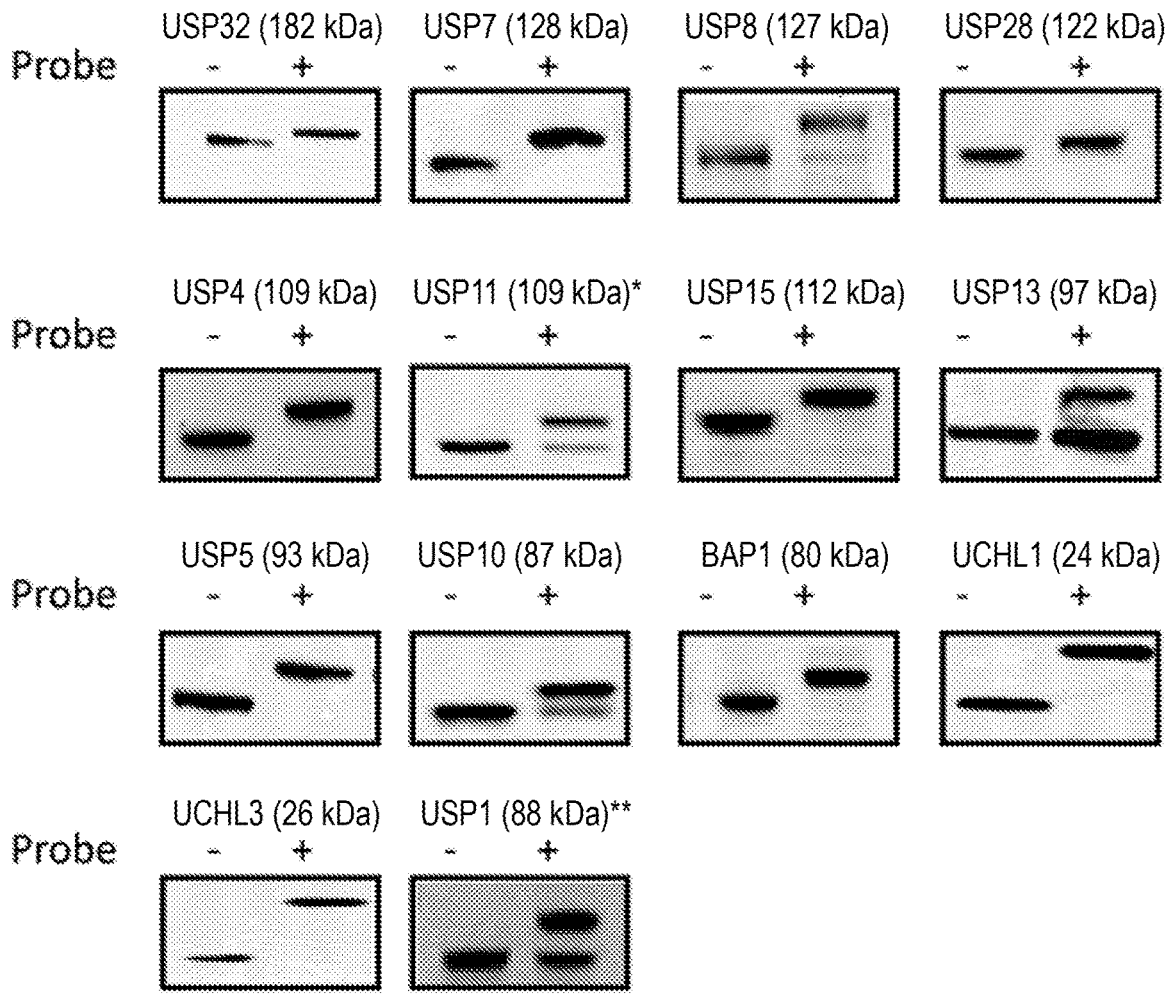
FIG. 5 shows examples of low-throughput activity probe assays developed in human cell lines to monitor inhibition of endogenous DUBs. Incubation of activity probe results in a complex with the isopeptidase, which results in slower migrating forms in SDS-PAGE. It can be seen that probe binding causes the position of the band to alter on the western blot. Unless stated, the activity probe used is Ub-VME and the cell line used is HEK 293. Key *=U2OS cells and **=CAL51 cells.
Figure 5:
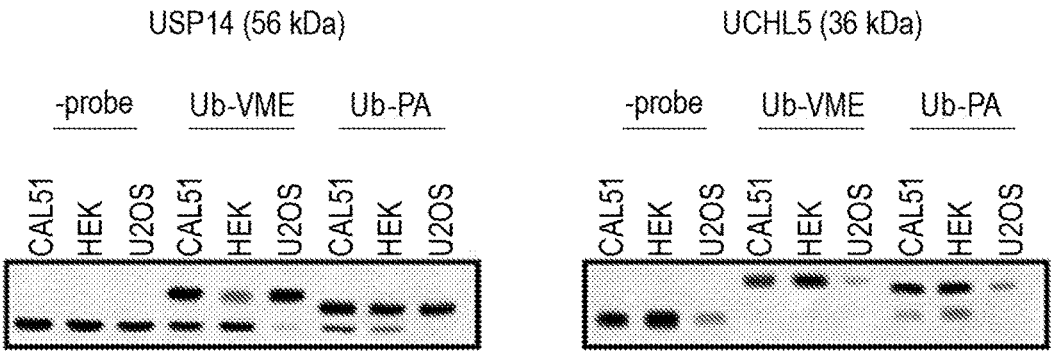

TABLE 1 list of antibodies used in FIG. 5 and in HTRF assays.

| Target | Supplier | Catalogue number | Lot number | Working Dilution |
|---|---|---|---|---|
| USP32 | Bethyl | A302-287A | A302-287A-1 | 1/2000 |
| USP7 | Abcam | ab4080 | GR6510-4 | 1/1000 |
| USP8 | Sigma | HPA004869 | B69519 | 1/1000 |
| USP28 | Novus Biologicals | NBP1-31171 | 39906 | 1/1000 |
| USP4 | Bethyl | A300-830A | A300-830A-1 | 1/1000 |
| USP11 | Bethyl | A301-613A | A301-613A-1 | 1/4000 |
| USP15 | Life sensors | AB517-50 | AB-39577.001 | 1/1000 |
| USP13 | Abcam | ab99421 | GR41410-7 | 1/1000 |
| USP5 | Bethyl | A301-542A | A301-542A-1 | 1/1000 |
| USP10 | Abcam | ab70895 | GR22660-6 | 1/1000 |
| BAP1 | Santa Cruz | sc-28383 | E1513 | 1/500 |
| UCHL1 | Cell Signalling | 3524S | 1 | 1/1000 |
| UCHL3 | Santa Cruz | sc-100340 | L2111 | 1/1000 |
| USP1 | Cell Signalling | 8033S | 1 | 1/2000 |
| UCHL5 | Abcam | ab124931 | GR82268 | 1/2000 |
| USP14 | Cell Signalling | 11931S | 1 | 1/2000 |

The invention will now be described in relation to the Examples, which are not limiting to the invention, and provide examples of isopeptidase assay, most notably deubiquitylating enzyme assays.

EXAMPLES (FIGURES EXPLANATIONS AND CONCLUSIONS)

Example 1 (FIG. 5)

The activity of a large number of endogenous DUBs can be monitored using the activity probe assay. Most of the DUBS will react fully with the Ub-VME probe (A) but some of them (typically USP14) are Ub-PA preferring DUBs (B). The optimisation of the conditions for each DUB is critical to obtain the best possible assay conditions. Although very low throughput, the immunoblot technology provides useful information, such as the ratio of unbound to probe bound protein and allows a number of DUBs of different sizes to be examined at the same time. A number of DUBs may be examined on the same blot. This experiment was done following the protocol described in the material and methods section "Standard ubiquitin-based activity probe immunoblot assay".

Example 2 (FIG. 6)

DUB activity can be monitored in animal tissues. Activity probe assays using tumour xenograft (A) versus surrogate tissue (B) is particularly useful to study the pharmacodynamics of compounds. The surrogate tissue used included brain, ovary, testes and xenograft (H226, A549 and H460) mouse tumours. This experiment was done following the protocol described in the material and methods section "Standard ubiquitin-based activity probe immunoblot assay" after the tissue lysate preparation described in the section "Preparation of tissue lysates".

Example 3 (FIG. 7)

Inhibition of endogenous USP11 by a small molecule inhibitor MTX078594 (MISSION Therapeutics, Cambridge, UK) is very stable. The inhibition of a USP11 remains intact after freezing the sample and prolonged storage at −80° C. The thawing process also did not alter the reactivity of the enzyme with the probe, even when the freezing medium did not contain glycerol. This experiment was done following the protocol described in the material and methods section "Standard ubiquitin-based activity probe immunoblot assay".

Example 4 (FIG. 8)

Optimisation of high throughput HTRF activity probe assays to monitor DUB activity. When optimising assays using exogenously expressed DUBs, it is important to assess multiple cell lines and expression levels of the DUBs, as determined by the amount of plasmid DNA and/or the length of time following transfection. The assay format shown on this panel is 96-well but can be applied to a 384-well format (not shown) allowing for a high throughput and on-target cellular assay. The HTRF signal is highly reproducible across biological replicates and can be evaluated across multiple cell lines. This experiment was done following the protocol described in the material and methods section "Standard HTRF ubiquitin-based activity probe assay", except that the amount of lysate was varied.

Example 5 (FIG. 9)

Optimising the HTRF activity probe assay is an important step towards robustness and reliability. Each component of the cellular HTRF activity probe assay must be titrated and the hook point determined (the concentration above which the effect on the HTRF signal is detrimental). FIG. 9A shows that the hook point for lysate concentration was not reached, allowing for more concentrated lysates to be used if required. The combinations of the detection antibodies helps to assess the best possible pair of antibodies (anti-FLAG donor and anti-HA acceptor in this case). FIG. 9B depicts that the hook point for the lysate concentration was not reached, but that the hook point for the Ub-VME probe was approximately 30 nM. This experiment was done following the protocol described in the material and methods section "Standard HTRF ubiquitin-based activity probe assay", with the exceptions of the permutation of the detection antibodies (acceptor and donor), the volume of lysates (1, 2, or 3.4 μg) or the time for which the cells were allowed to express the transgene before the assay was performed (24 h or 48 h).

Example 6 (FIG. 10)

HTRF activity probe $IC_{50}$ assays in cells exogenously expressing a DUB can be performed using detection reagents targeting the tag (anti-FLAG) or specific protein (anti-USP11). In addition, the high degree of correlation between the two assays following treatment of the cells with various small molecule inhibitors reinforces the strength of the HTRF technology. These results demonstrate the feasibility to monitor the activity of endogenous DUBs in human tissues, for pharmacologic studies or diagnostic purposes. This experiment was done following the protocol described in the material and methods section "Standard HTRF ubiquitin-based activity probe assay", with the alternative 1 used for the right hand panel.

Example 7 (FIG. 11)

Validation requires benchmarking the cellular HTRF activity probe assays against traditional biochemical (enzymatic) assays. In the example shown in FIG. 11A, two compounds showed a remarkable correlation: high potencies in both the biochemical FP assay (using purified FLAG-UCHL1) and the cellular HTRF activity probe assay (using cells expressing FLAG-UCHL1). FIG. 11B demonstrates a very good correlation between both assays for more than 150 compounds. The biochemical and cellular $IC_{50}$ determinations were done following the protocols described in the material and methods sections "FLAG-UCHL1 biochemical assay" and "Standard HTRF ubiquitin-based activity probe assay".

Example 8 (FIG. 13)

HTRF activity probe $IC_{50}$ assays in U2OS cells can be performed using detection reagents targeting the endogenous USP11 protein. The comparison between the low throughput immunoblotting method and the high throughput HTRF methods is shown. The same samples were processed using the HTRF method (top panel), as described in the material and methods section "Standard HTRF ubiquitin-based activity probe assay—alternative 1" and using the immunoblot methods as described in "Standard ubiquitin-based activity probe immunoblot assay". The values obtained after the quantification were plotted to calculate the $IC_{50}$.

Example 9 (FIG. 14)

An example of optimisation of the HTRF assay measuring the endogenous USP5 activity using HTRF in HEK 293 cells is shown. HEK 293 cells were cultivated in 2-15 cm dishes and the lysates made as described in the material and methods section "Standard HTRF ubiquitin-based activity probe assay". No compound was used in this experiment but the impact of the lysate concentration, the dilution of the secondary antibody that recognises the anti-USP5 antibody (Bethyl A301-542A) and the concentration of the Ub-VME probe was assessed. 0.05 μL of anti-USP5 was added per well. This shows that optimising the conditions of the assay greatly improves the assay window.

Example 10 (FIG. 15)

This example demonstrates that target engagement can be measured by a HTRF activity probe assay in tissues. The brain surrogate tissue and the SW48 tumour tissue were removed from the mouse and prepared as described in the methods section "Preparation of tissue lysates". After quantification, 10 μg of the lysates were incubated for 30 min at RT with the known inhibitors PR-619 (Sigma—SML0430) or ubiquitin aldehyde (Boston Biochem—U201) at various concentrations in order to generate $IC_{50}$ curves. The rest of the assay is described in the methods section "Standard HTRF ubiquitin-based activity probe assay" alternative 1. Details of the reagents amounts or final concentrations are as follow: Ub-VME probe: 75 nM, anti-USP5 (Bethyl—A301-542A): 0.05 μL per well, anti-rabbit-cryptate (Cisbio #61PARKLA): 0.02 μL per well and anti-HA-XL (Cisbio #610HAXLB): 0.1 μL per well.

Sequences

| Isopeptidase | GenPept Database NCBI Reference Sequence including Version Number | GenBank Database NCBI Reference Sequence including Version Number |
| --- | --- | --- |
| USP11 | NP_004642.2 | NM_004651.3 |
| USP4 | NP_003354.2 | NM_003363.3 |
| UCHL1 | NP_004172.2 | NM_004181.4 |
| USP7 | NP_003461.2 | NM_003470.2 |
| UCHL3 | NP_001257881.1 | NM_001270952.1 |
| UCHL5 | NP_057068.1 | NM_015984.3 |
| BAP1 | NP_004647.1 | NM_004656.3 |
| USP1 | NP_003359.3 | NM_003368.4 |
| USP10 | NP_001259004.1 | NM_001272075.1 |
| USP5 | NP_001092006.1 | NM_001098536.1 |
| USP13 | NP_003931.2 | NM_003940.2 |
| USP15 | NP_001239007.1 | NM_001252078.1 |
| USP28 | NP_065937.1 | NM_020886.2 |
| USP8 | NP_005145.3 | NM_005154.4 |
| USP32 | NP_115971.2 | NM_032582.3 |
| USP14 | NP_005142.1 | NM_005151.3 |

NCBI website.

The invention claimed is:
1. A high throughput method for determining the activity of an isopeptidase enzyme in a biological sample, comprising the steps of:
  i) preparing an extract of said sample;
  ii) contacting the extract with an activity probe;
  iii) including reagents which bind to or interact with at least one of the activity probe or the enzyme, and generate a detectable signal; and
  iv) measuring the detectable signal,
wherein said reagents which bind to or interact with the at least one of the activity probe or the enzyme comprise at least two separate binding agents, one of which binds to the activity probe, and one of which binds to the isopeptidase enzyme.

2. A method as claimed in claim 1 which is suitable for diagnosing or prognosing a disease, disorder or condition associated with a defective isopeptidase.

3. A method as claimed in claim 1 which is suitable for diagnosing or prognosing an infection with a microorganism by determining the activity of an isopeptidase enzyme from the microorganism.

4. A method as claimed in claim 1 which is suitable for determining the activity of an isopeptidase in the presence of a putative inhibitor, comprising an additional step of treating the biological sample with the putative inhibitor.

5. A method as claimed in claim 1 which is suitable for determining the potency of a putative inhibitor, comprising an additional step of treating the biological sample with the putative inhibitor.

6. A method as claimed in claim 1 which is suitable for determining the pharmacodynamics of a putative inhibitor, comprising the following additional steps:
   a) treating an animal with said putative inhibitor
   b) removing a biological sample from said animal.

7. A method as claimed in claim 1 wherein the activity probe comprises one or more of:
   a) Ubiquitin or a Ubiquitin-like molecule;
   b) a warhead; or
   c) a tag.

8. A method as claimed in claim 7 wherein the warhead binds to or interacts with an active site of the isopeptidase enzyme.

9. A method as claimed in claim 8 wherein the warhead is selected from an alkyl halide or propargyl (PA).

10. A method as claimed in claim 1 wherein the detectable signal is generated if the activity probe has hound to the isopeptidase enzyme.

11. A method as claimed in claim 1, wherein said reagents which bind to or interact with the at least one of the activity probe or the enzyme comprise reagents that are labelled, such that a signal is generated if the activity probe has bound to the isopeptidase enzyme.

12. A method as claimed in claim 1 wherein said isopeptidase is endogenous to the biological tissue.

13. A method as claimed in claim 1 wherein said isopeptidase enzyme is exogenous to the biological sample.

14. A method as claimed in claim 13 wherein said exogenous isopeptidase enzyme has been transfected.

15. A method as claimed in claim 1 wherein said isopeptidase enzyme is a deubiquitylating enzyme.

16. A method as claimed iii claim 1 wherein said biological sample contains comprises cells.

17. A method as claimed in claim 3 wherein said biological sample comprises cells of the microorganism.

18. A method as claimed in claim 1 wherein said extract is plated prior to being contacted with the activity probe.

19. A method as claimed in claim 1 wherein the detectable signal generated includes light at any wavelength.

20. A method as claimed in claim 1 wherein said biological sample is taken from a human or animal treated with a putative inhibitor of said isopeptidase enzyme.

21. A kit for use in assessing the activity of an isopeptidase enzyme in a biological sample in a high throughput format, the kit comprising an activity probe and detection reagents, wherein said reagents, which bind to or interact with said activity probe or the enzyme, comprise at least two separate binding agents, one of which binds to the activity probe, and one of which binds to the isopeptidase enzyme.

22. A method as claimed in claim 9 wherein the warhead comprises chloroethyl, bromoethyl, bromopropyl, vinyl methyl ester, vinyl methyl sulfone, vinyl phenyl sulfone, or vinyl cyanide group.

* * * * *